(12) United States Patent
Bae et al.

(10) Patent No.: US 11,931,401 B2
(45) Date of Patent: Mar. 19, 2024

(54) RUNX3 MODIFIED PROTEIN FOR PREVENTION OR TREATMENT OF CANCER

(71) Applicant: GeneCraft Inc., Cheongju-si (KR)

(72) Inventors: Suk Chul Bae, Cheongju-si (KR); Jung Won Lee, Daejeon (KR); You Soub Lee, Cheongju-si (KR)

(73) Assignee: GeneCraft Inc., Cheongju-si (KR)

( * ) Notice: Subject to any disclaimer, the term of this patent is extended or adjusted under 35 U.S.C. 154(b) by 211 days.

(21) Appl. No.: 17/239,289

(22) Filed: Apr. 23, 2021

(65) Prior Publication Data

US 2021/0330740 A1  Oct. 28, 2021

(30) Foreign Application Priority Data

Apr. 23, 2020  (KR) .................. 10-2020-0049341
Dec. 28, 2020  (KR) .................. 10-2020-0184526

(51) Int. Cl.
| | |
|---|---|
| *A61K 38/17* | (2006.01) |
| *A61K 31/436* | (2006.01) |
| *A61K 31/519* | (2006.01) |
| *A61K 47/46* | (2006.01) |
| *A61P 35/00* | (2006.01) |
| *C07K 14/47* | (2006.01) |
| *C12N 7/00* | (2006.01) |

(52) U.S. Cl.
CPC ............ *A61K 38/17* (2013.01); *A61K 31/436* (2013.01); *A61K 31/519* (2013.01); *A61K 38/1709* (2013.01); *A61K 47/46* (2013.01); *A61P 35/00* (2018.01); *C07K 14/4702* (2013.01); *C12N 7/00* (2013.01); *C12N 2750/14143* (2013.01)

(58) Field of Classification Search
CPC ........................................ A61K 38/17
See application file for complete search history.

(56) References Cited

U.S. PATENT DOCUMENTS

| | | | | |
|---|---|---|---|---|
| 2008/0261883 | A1* | 10/2008 | Bae ................. | A61P 11/00 514/44 R |
| 2012/0128642 | A1 | 5/2012 | Teumer et al. | |
| 2015/0336967 | A1 | 11/2015 | Czardybon et al. | |
| 2018/0002393 | A1* | 1/2018 | Bancel ............ | A61K 48/0033 |

FOREIGN PATENT DOCUMENTS

| | | | |
|---|---|---|---|
| KR | 10-1994957 | 6/2019 | |
| WO | WO2013151672 | * 10/2013 | ............ C12N 15/85 |

OTHER PUBLICATIONS

Strausberg et al. (Generation and initial analysis of more than 15,000 full-length human and mouse cDNA sequences Journal Proc. Natl. Acad. Sci. U.S.A. 99 (26), 16899-16903 (2002)) (Year: 2002).*
Sequence Alignment of SEQ ID No. 3 (17239289) with SEQ ID No. 3744 (WO2013/151672) (Year: 2022).*
Anas El-Aneed (Journal of Controlled Release. 2004; 9:1-14) (Year: 2004).*
Zhang et al. PTHrP prevents chondrocyte premature hypertrophy by inducing cyclin-D1-dependent Runx2 and Runx3 phosphorylation, ubiquitylation and proteasomal degradation. J Cell Sci. May 1, 2009;122(Pt 9):1382-9. doi: 10.1242/jcs.040709. Epub Apr. 7, 2009. (Year: 2009).*
Sequence alignment of SEQ ID No. 2 (17239289) with SEQ ID No. 8280 (15425813); Sequence alignment of SEQ ID No. 4 (17239289) with SEQ ID No. 1 (12051649) (Year: 2022).*
Berns, "Cancer: The blind spot of p53," *Nature* 468.7323: 519-520, Nov. 2010.
Feldser et al., "Stage-specific sensitivity to p53 restoration during lung cancer progression," *Nature* 468.7323: 572-575, Nov. 2010.
Ito et al., "The RUNX family: developmental regulators in cancer," *Nature Reviews Cancer* 15: 81-95, Jan. 2015.
Junttila et al., "Selective activation of p53-mediated tumour suppression in high-grade tumours," *Nature* 468.7323: 567-571, Nov. 2010.
Lee et al., "Runx3 is required for the differentiation of lung epithelial cells and suppression of lung cancer," *Oncogene* 29: 3349-3361, Mar. 2010.
Lee et al., "Runx3 Inactivation is a Crucial Early Event in the Development of Lung Adenocarcinoma," *Cancer Cell* 24: 603-616, Nov. 2013.
Lee et al., "RUNX3 protects against oncogenic KRAS," *Cancer Discovery* 4.1: Jan. 14, 2014.
Lee et al., "RUNX3 regulates cell cycle-dependent chromatin dynamics by functioning as a pioneer factor of the restriction-point," *Nat Commun.* 10: 1897, 2019 (17 pages).
"Study on the decision making mechanism for cell division," Final (Result) Report of Research Fellow for Academic Successor Generation Project, 2017 (w/English translation of summary of research results).
Walter et al., "RB constrains lineage fidelity and multiple stages of tumour progression and metastasis," *Nature* 569.7756: 423-427, May 2019 (w/supplemental information).

(Continued)

Primary Examiner — Allison M Fox
Assistant Examiner — Alyssa G Weston
(74) Attorney, Agent, or Firm — Klarquist Sparkman, LLP

(57) ABSTRACT

In the present invention, it was confirmed that the modified protein in which the 356th serine of Runx3 is substituted with alanine has an increased activity of maintaining the complex with Brd2 by more than 10 times compared to the wild-type Runx3, and the apoptosis effect is improved in various cancer cell lines compared to the wild-type Runx3. Therefore, the modified protein in which the 356th serine of Runx3 is substituted with an amino acid that cannot be phosphorylated by a kinase of the present invention, the polynucleotide coding thereof, the vector carrying the polynucleotide, or the virus or cell transformed with the vector can be used as a therapeutic agent for various cancers.

11 Claims, 17 Drawing Sheets

Specification includes a Sequence Listing.

(56) References Cited

OTHER PUBLICATIONS

Wang et al., "Comparison of Adenoviral and Adeno-Associated Viral Vectors for Pancreatic Gene Delivery In Vivo," *Hum Gene Ther. 15.4*: 405-413, Apr. 2004.
Wang et al., "Targeting adeno-associated virus and adenoviral gene therapy for hepatocellular carcinoma," *World J Gastroenterol. 22.1*: 326-337, Jan. 2016.

\* cited by examiner

```
MRIPYOPSTSRRFTPPSPXFPCDGGGGXMGEHSGALSXQAAVGPGGRAPP    #  50
EVRSMVDVLADHAGELYRTDSPNFLCSYLPSMMRCNKTLPVAFKYVALGD    # 100
YPDGTYYTYMAGNIDEHYSXELPMASAVMKNDVARFNDLRFYGPSGRGXSF   # 150
TLTITVFTMPTQVATVHRXIKYTVDGPREPRXHRQXLEDQTKPFPDRFQD    # 200
LERLPMRYTPSTPSPRGSLSTTSHFSSQPQTPIQGTSELMPFSDPRGFDR    # 250
SFPTLPTLTESRFRDPRMHYPGXMSXAFPYSXTPSGTSISSLSYAGMPXT    # 300
SRFHHTYLPPPYPGXPQMQSGPFQXNPSPYHLYVGTSSGSYQFSMVAGSS    # 350
SGGDRXTRMLXSCTSSXASVXAGMLMMPSLGDQSDGYEXDGSHSMSPTX     # 400
LSTPGRMDEAVMRPY                                       # 450
........STS...T..S..........................         #  50
...S..............T..S.....S...S...........          # 100
......................V.....................S....S.  # 150
..T......T..T...............................         # 200
........T.ST.S...S.STT...SS....T..........            # 250
.....................S.......T.S.TS..S.S......T     # 300
S....T...........S........S........TS..SY..S....SS   # 350
S....S.T.......T....S...............S.......S.S.S... # 400
.ST..↑.........                                       
```

```
MRIPVDPSTSRRFTPPSPAFPCGGGGGKMGENSGALSAQAAVGPGGRARP    #  50
EVRSMVDVLADHAGELVRTDSPNFLCSVLPSHWRCNKTLPVAFKVVALGD    # 100
VPDGTVYTVMAGNDENYSAELRNASAVMKNQVARFNDLRFVGRSGRGKSF    # 150
TLTITVFTNPTQVATVHRAIKVTVDGPREPRRHRQKLEDQTKPFPDRFGD    # 200
LERLRMRVTPSTPSPRGSLSTTSHFSSQPQTPIQGTSELNPFSDPRGFDR    # 250
SFPTLPTLTESRFPDPRMHYPGAMSAAFPYSATPSGTSISSLSVAGNPAT    # 300
SRFHHTVLPPPYPGAPQNQSGPFQANPSPYHLVYGTSSGSYQFSMVAGSS    # 350
SGGDRAPTRMLASCTSSAASVAAGNLMNPSLGGQSDGVEADGSHSNSPTA    # 400
LSTPGRMDEAVWRPY                                       # 450
.......STS...T..S.................................   #  50
...S................T.S.....S...S.................   # 100
......................V......................S....S. # 150
..T......T...T....................................   # 200
........T.ST.S....S.STT...SS...T..................   # 250
..................S........T.S.TS..S.S.....T       # 300
S....T...........S........S.......TS..SY..S....SS    # 350
S.....T......T....S................S......S.S.S...   # 400
.ST..T.........                                       
```

```
MRIPVDPSTSRRFTPPSPAFPCGGGGGKMGENSGALSAQAAVGPGGRARP    #  50
EVRSMVDVLADHAGELVRTDSPNFLCSVLPSHWRCNKTLPVAFKVVALGD    # 100
VPDGTVVTVMAGNDENVSAELRNASAVMKNQVARFNDLRFVGRSGRGKSF    # 150
TLTITVFTNPTQVATYHRAIKYTVDGPREPRRHRQKLEDQTKPFPDRFGD    # 200
LERLRMRVTPSTPSPRGSLSTTSHFSSQPQTPIDGTSELNPFSDPRQFDR    # 250
SFPTLPTLTESRFPDPRMHVPGAMSAAFPYSATPSGTSISSLSVAGMPAT    # 300
SRFHHTVLPPPYPGAPQNQSGPFQANPSPYHLVYGTSSGSYQFSMYAGSS    # 350
SGGDRIPTRMLASCTSSAASVAAGNLMNPSLGGQSDGYEADGSHSNSPTA    # 400
LSTPGHMDEAVWRPY                                      # 450
.......STS...T..S.................................  #  50
...S............T.S.....S...S.....................  # 100
..............V..........................S....S..  # 150
..T.......T...T...................................  # 200
........T.ST.S...S.STT...SS...T...................  # 250
........................S.......T.S.TS...S.S......T # 300
S....T..........S........S......TS..SV..S....SS    # 350
S....↑T....S.T....S..............S.......S.S.S...  # 400
.ST..↑.........                                      
```

MRIPVDPSTSRRFTPPSPAFPCGGGGGKNGENSGALSADAAVGPGGRARP    #  50
EVRSNVDVLADHAGELVRTDSPNFLCSVLPSHWRCNKTLPVAFKVYALGD    # 100
VPDGTYVTYMAGNDENYSAELRNASAVMKNDYARFNDLRFVGRSGRGKSF    # 150
TLTITYFTNPTQVATYHRAIKVTVDGPREPRRHRQKLEDQTKPFPDRFGD    # 200
LERLRMRVTPSTPSPRGSLSTTSHFSSQPQTPIQGTSELNPFSDPRQFDR    # 250
SFPTLPTLTESRFPDPRMHVPGAMSAAFPYSATPSGTSISSLSVAGMPAT    # 300
SRFHHTYLPPPYPGAPQNDSGPFQANPSPYHLYYGTSSGSYQFSMVAGSS    # 350
SGGDFLPTRMLASCTSSAASVAAGNLMNPSLGGQSDGVEADGSHSNSPTA    # 400
LSTPGRNDEAVWRPV                                       # 450
......STS...T..S..................................    #  50
...S............T.S.....S..S......................    # 100
................Y..........................S....S.   # 150
..T......T...T....................................    # 200
........T.ST.S...S.STT...SS...T....................   # 250
........................S.........T.S.TS..S.S......T # 300
S....T............S.........S.......TS..SV..S....SS  # 350
S...↑.....S.T....S............S......S.S.S...        # 400
.ST..↑........                                        
```

```
MRIPVDPSTSRRFTPPSPAFPCGGGGGKMGENSGALSAQAAVGPGGRARP    #    50
EYRSMVDVLADHAGELYRTDSPNFLCSVLPSHWRCNKTLPVAFKYVALGD    #   100
VPDGTVYTVMAGNDENYSAELRNASAVMKNDVARFNDLRFVGRSGRGKSF    #   150
TLTITVFTNPTQVATVHRAIKVTVDGPREPRPHRQKLEDQTKPFPDRFGD    #   200
LERLRMRVTPSTPSPRGSLSTTSHFSSQPQTPIQGTSELNPFSDPRQFDR    #   250
SFPTLPTLTESRFPDPRMHVPGAMSAAFPVSATPSGTSISSLSVAGMPAT    #   300
SRFHHTYLPPPYPGAPQNQSGPFQANPSPYHLYYGTSSGSYQFSMVAGSS    #   350
SGGDRYPTRMLASCTSSAASVAAGNLMNPSLGGQSDGVEADGSHSNSPTA    #   400
LSTPGRMDEAVWRPV                                       #   450
......STS...T..S..................................    #    50
...S............T.S.....S...S.....................    #   100
.................V........................S....S.    #   150
..T......T...T....................................    #   200
........T.ST.S...S.STT...SS...T...................    #   250
.........................S........T.S.TS..S.S.....T   #   300
S....T............S........S........TS..SY..S....SS  #   350
S.....T......T....S................S.......S.S.S...  #   400
.ST..T...........                                     #
```

RUNX3 MODIFIED PROTEIN FOR PREVENTION OR TREATMENT OF CANCER

CROSS REFERENCE TO RELATED APPLICATIONS

This application claims the benefit of priority from Korean Patent Application No. 10-2020-0049341, filed on Apr. 23, 2020, and Korean Patent Application No. 10-2020-0184526, filed on Dec. 28, 2020, the contents of each of which are incorporated herein by reference.

BACKGROUND OF THE INVENTION

1. Field of the Invention

The present invention relates to a pharmaceutical composition comprising a Runx3 modified protein as an active ingredient for prevention or treatment of cancer.

2. Description of the Related Art

Research on the development of targeted cancer therapy is focused on strategies to control cancer cells by inhibiting the function of an oncogene or activating the function of a tumor suppressor gene. Abnormal activation of K-Ras function by mutation of K-Ras among the oncogenes is known as one of the major causes of human cancer. The mutation of K-Ras is also observed in lung cancer, and it is known that the mutation of K-Ras is observed in about 35% of lung adenocarcinoma. Thus, in order to treat cancer caused by the activation of K-Ras function, studies have been conducted on a method of treating cancer by inhibiting the function of K-Ras. However, a strategy that directly inhibits the function of K-Ras has not been developed as a successful anticancer drug because it causes serious damage to normal cells. Therefore, instead of suppressing the function of an oncogene, a strategy of activating the inhibited function of a tumor suppressor gene is receiving attention. Therefore, instead of a strategy for inhibiting the function of an oncogene, a strategy for activating the inhibited function of a tumor suppressor gene is attracting attention.

The said tumor suppressor gene refers to a nucleotide sequence that can be expressed in a target cell to suppress a tumor phenotype or induce apoptosis. The tumor suppressor genes identified so far include sPD-1, VHL, MMAC1, DCC, p53, NF1, WT1, Rb, BRCA1 and BRCA2. Among them, it has been reported that p53 or Rb gene is frequently inhibited in its function in K-Ras mutant cancers. Whether it is possible to treat K-Ras mutant cancer through the repair of the suppressor gene has become a subject of great interest in the field of anticancer agent development research. Accordingly, there have been attempts to treat K-Ras mutant lung adenocarcinoma by recovering the function of p53 gene, which is a representative tumor suppressor gene, but it was not successful because early lung adenocarcinoma was not cured (Feldser, D. M. et al., Nature, 468: 572-575, 2010, Junttila, M. R. et al., Nature, 468: 567-571, 2010). In addition, it was found that K-Ras mutant lung cancer could not be cured through the recovery of Rb gene function (Walter, D. M. et al. Nature 2019). The above results indicate that even if the function of the tumor suppressor gene is simply restored, the therapeutic effect on the already-onset cancer does not appear, because the early stage cancer rapidly develops into a malignant cancer (Berns A., Nature, 468:519-520, 2010). There have been no reports of successful treatment of K-Ras mutant lung cancer through the activation of a tumor suppressor gene.

It has been reported that the function of Runx3 gene as a tumor suppressor gene is inhibited in K-Ras mutant cancers (RUNX3 Protects against Oncogenic KRAS. (2013). Cancer Discovery, 4(1), 14-14), and that the activity of Runx3 gene is inhibited in lung adenocarcinoma caused by the mutation of K-Ras (Lee, K. S., Lee, Y. S., Lee, J. M., Ito, K., Cinghu, S., Kim, J. H., Bae, S. C. Oncogene, 29(23): 3349-61, 2010).

Runx3, a transcription factor that binds to DNA, plays a crucial role in lineage determination (Ito, Y., Bae, S. C. & Chuang, L. S. The RUNX family: developmental regulators in cancer. Nat. Rev. Cancer 15, 81-95 (2015)). Deletion of Runx3 in the mouse lung leads to the development of lung adenomas and accelerates the progression to adenocarcinoma (ADCs) induced by K-Ras.

Thus, the present inventors have completed the present invention by confirming that the modified protein in which the $356^{th}$ serine of Runx3 is substituted with alanine has an increased activity of maintaining the complex with Brd2 compared to the wild-type Runx3, and the apoptosis effect is improved in various cancer cell lines compared to the wild-type Runx3.

SUMMARY OF THE INVENTION

It is an object of the present invention to provide a pharmaceutical composition comprising a Runx3 modified protein as an active ingredient for prevention or treatment of cancer.

To achieve the above object, the present invention provides a pharmaceutical composition for prevention or treatment of cancer, comprising a modified protein in which the $356^{th}$ serine of Runx3 (Runt-related transcription factor 3) is substituted with a hydrophobic amino acid, a polynucleotide coding thereof, a vector carrying the polynucleotide, or a virus or cell transformed with the vector as an active ingredient.

Advantageous Effect

In the present invention, it was confirmed that the modified protein in which the $356^{th}$ serine of Runx3 is substituted with alanine has an increased activity of maintaining the complex with Brd2 by more than 10 times compared to the wild-type Runx3, and the apoptosis effect is improved in various cancer cell lines compared to the wild-type Runx3. Therefore, the modified protein in which the $356^{th}$ serine of Runx3 is substituted with an amino acid that cannot be phosphorylated by a kinase of the present invention, the polynucleotide coding thereof, the vector carrying the polynucleotide, or the virus or cell transformed with the vector can be used as a therapeutic agent for various cancers.

BRIEF DESCRIPTION OF THE DRAWINGS

FIGS. 2a and 2b are a sequence and a diagram illustrating the predicted degree of phosphorylation of the wild-type protein in which the $356^{th}$ serine of Runx3 is not substituted, confirming that the phosphorylation occurred in the $356^{th}$ serine. The sequence shown in FIG. 2a is SEQ ID NO: 2.

FIGS. 2c and 2d are a sequence and a diagram illustrating the predicted degree of phosphorylation of S356A, in which the 356$^{th}$ serine of Runx3 is substituted with alanine, confirming that the phosphorylation did not occur in the 356$^{th}$ alanine. The sequence shown in FIG. 2c is SEQ ID NO: 2 with a S356A substitution.

FIGS. 2e and 2f are a sequence and a diagram illustrating the predicted degree of phosphorylation of S356I, in which the 356$^{th}$ serine of Runx3 is substituted with isoleucine, confirming that the phosphorylation did not occur in the 356$^{th}$ isoleucine. The sequence shown in FIG. 2e is SEQ ID NO: 2 with a S356I substitution.

FIGS. 2g and 2h are a sequence and a diagram illustrating the predicted degree of phosphorylation of S356L, in which the 356$^{th}$ serine of Runx3 is substituted with leucine, confirming that the phosphorylation did not occur in the 356$^{th}$ leucine. The sequence shown in FIG. 2g is SEQ ID NO: 2 with a S356L substitution.

FIGS. 2i and 2j are a sequence and a diagram illustrating the predicted degree of phosphorylation of S356V, in which the 356$^{th}$ serine of Runx3 is substituted with valine, confirming that the phosphorylation did not occur in the 356$^{th}$ valine. The sequence shown in FIG. 2i is SEQ ID NO: 2 with a S356V substitution.

SEQUENCE

Figure 1:
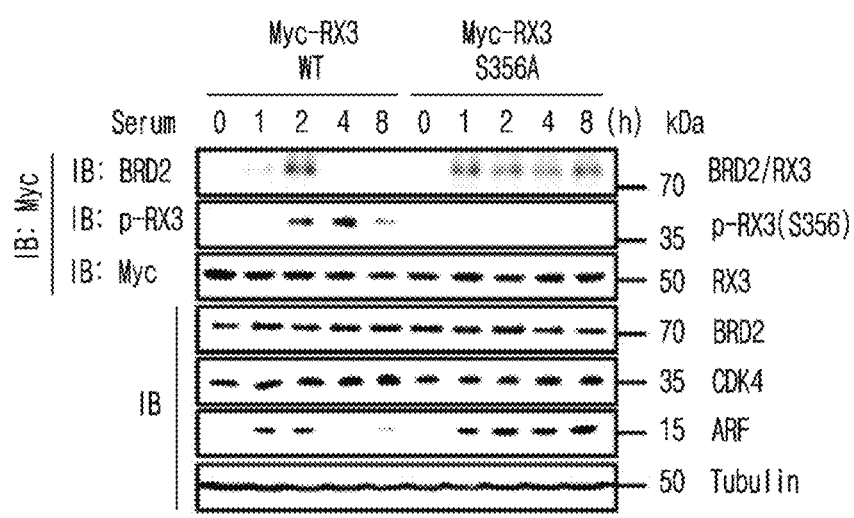
FIG. 1 is a diagram illustrating the time-dependent formation of a BRD2-RUNX3 complex and the RUNX3 phosphorylation in Ser-356 measured by immunoprecipitation (IP) and immunoblotting (IB), confirming that the binding between the overexpressed Myc-RUNX3-S356A and BRD2 was maintained until 8 hours after the serum stimulation.
Figure 2B:
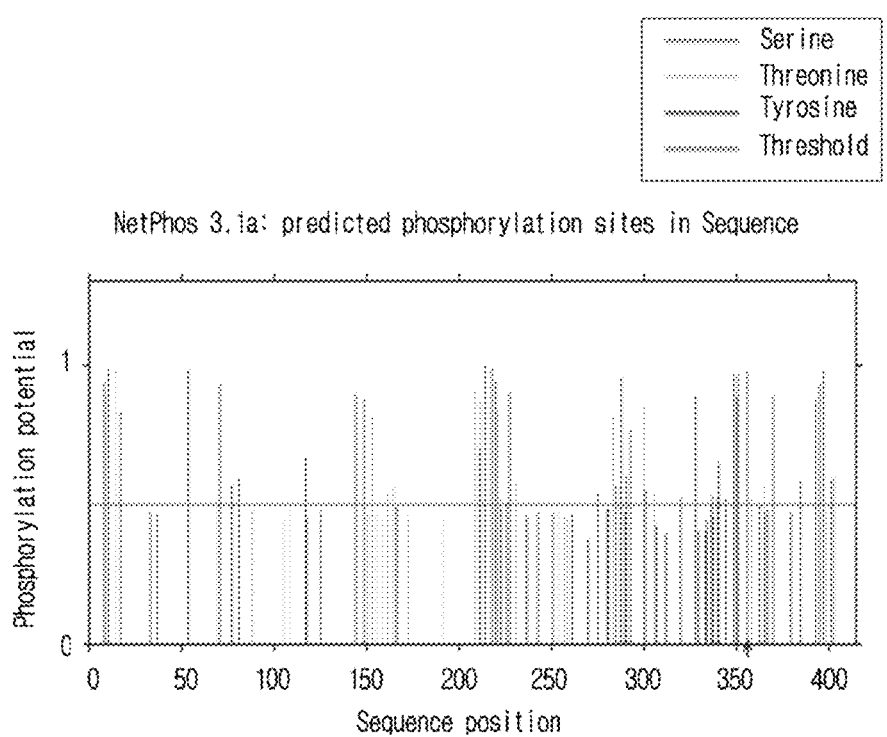
Figure 2D:
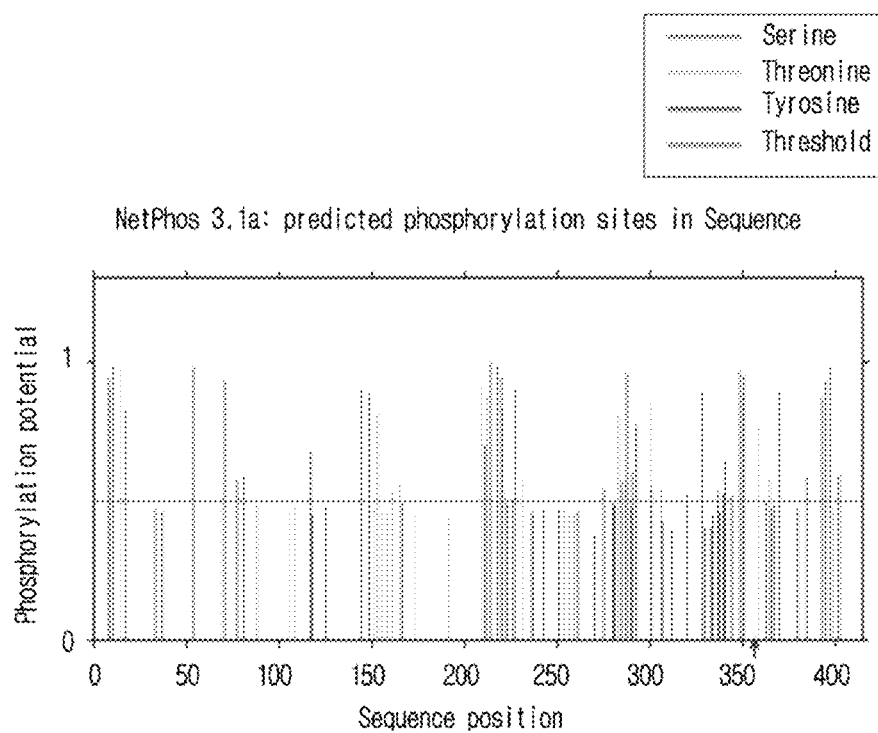
Figure 2F:
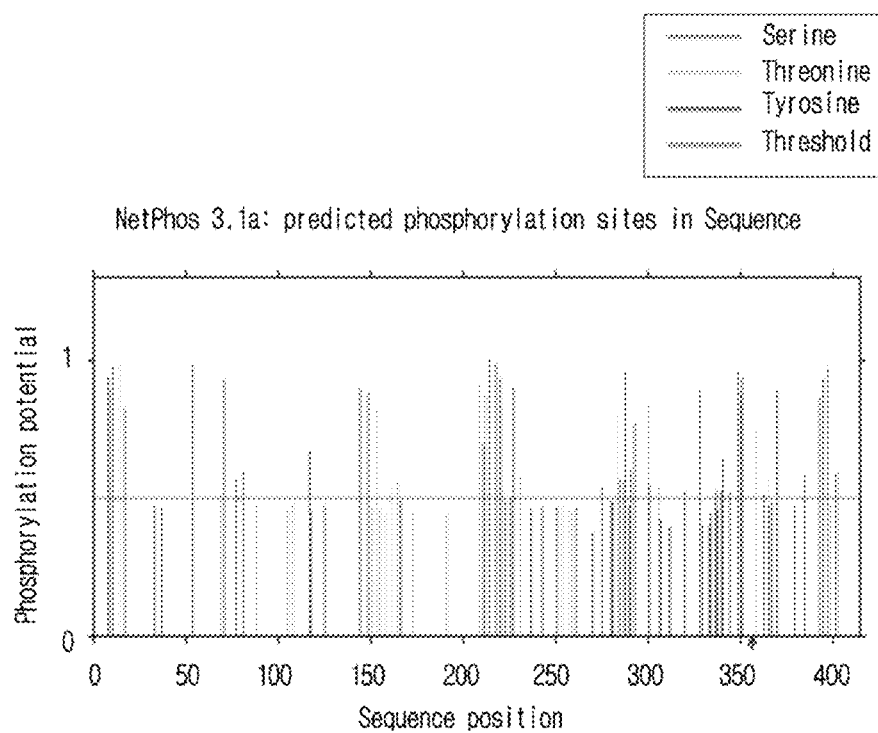
Figure 2H:
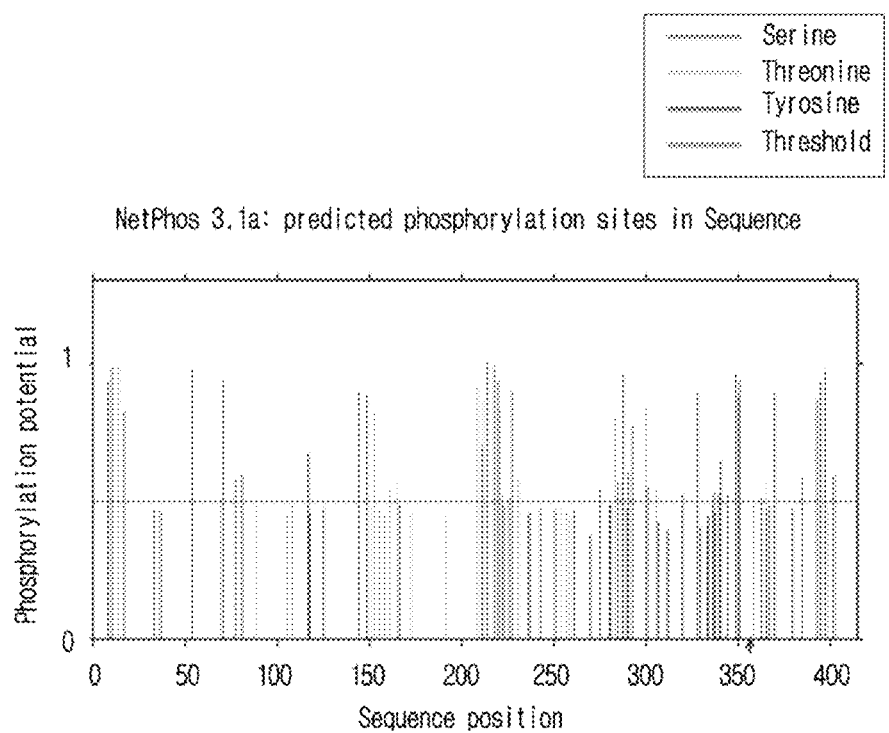
Figure 2J:
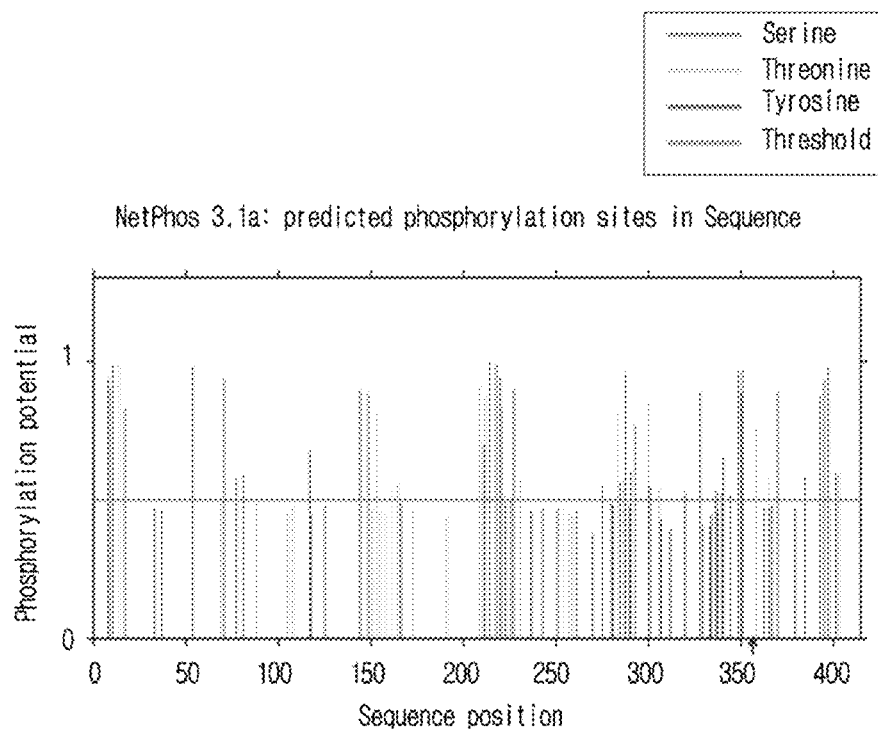

The Sequence Listing is submitted as an ASCII text file in the form of the file name "Sequence.txt" (~22 kb), which was created on Apr. 22, 2021, and which is incorporated by reference herein.

DESCRIPTION OF THE PREFERRED EMBODIMENTS

Hereinafter, the present invention is described in detail.

The present invention provides a pharmaceutical composition for prevention or treatment of cancer, comprising a modified protein in which the 356$^{th}$ serine of Runx3 (Runt-related transcription factor 3) is substituted with an amino acid that cannot be phosphorylated by a kinase, a polynucleotide coding thereof, a vector carrying the polynucleotide, or a virus or cell transformed with the vector as an active ingredient.

The cancer is solid cancer.

The solid cancer can be one or more selected from the group consisting of lung cancer, pancreatic cancer, liver cancer and stomach cancer, but not always limited thereto.

The amino acid that cannot be phosphorylated by a kinase can be one or more selected from the group consisting of alanine (A), isoleucine (I), leucine (L) and valine (V), but not always limited thereto.

Runx3 (Runt-related transcription factor 3) gene is one of the Runt family genes consisting of Runx1, Runx2 and Runx3. The Runt family genes play an important role in normal development and oncogenesis, and they function as transcriptional regulators of the Smad family, a downstream factor that mediates TGF-β and its signaling. Runx1 plays an important role in mammalian hematopoiesis, Runx2 plays an important role in bone formation, and Runx3 is mainly expressed in granular gastric mucosal cells, and plays a role in inhibiting cell differentiation of gastric epithelium. These three genes are located at loci of chromosomes 1p, 6p and 21q, of which Runx3 gene is located at 1p36. 11-1p36. 13. The Runx3 locus is one of the sites that are lost in a variety of cancers or affected by hemizygous defects. In addition, Runx3 has been found to be inactivated in various types of cancer, and it is gaining spotlight as a new target for the development of anticancer agents. As such, Runx3 is known to act as a tumor suppressor gene that suppresses the formation of cancer, and plays an important role in the restriction-point, which determines the fate of cell division and death, and induces cell division or apoptosis depending on the situation (Lee et al., Nat Commun. 2019; 10(1): Runx3 regulates cell cycle-dependent chromatin dynamics by functioning as a pioneer factor of the restriction-point). When a K-Ras oncogene mutation occurs in lung epithelial cells, Runx3 kills cancer cells by contributing to determining apoptosis fate at the restriction-point (Lee et al., Nat Commun. 2019; 10(1)).

A Runx3 protein refers to a Runt-related transcription factor 3 related to the Runt family expressed by the Runx3 gene.

The Runx3 protein can be composed of the amino acid sequence represented by SEQ. ID. NO: 1 or SEQ. ID. NO: 2.

The Runx3 protein can be derived from humans or animals.

The Runx3 protein can be synthesized by the conventional chemical synthesis method in the art (W. H. Freeman and Co., Proteins; structures and molecular principles, 1983), or can be prepared by the conventional genetic engineering method (Maniatis et al., Molecular Cloning: A laboratory Manual, Cold Spring Harbor laboratory, 1982; Sambrook et al., Molecular Cloning: A Laboratory Manual et al.).

The Runx3 protein can be a variant of an amino acid sequence having a different sequence by deletion, insertion or substitution of amino acid residues, or a combination thereof within a range that does not affect the function of the protein. Amino acid exchanges in proteins that do not totally alter the activity of the molecule are informed in the art. In some cases, the amino acid can be modified by phosphorylation, sulfation, acrylation, glycosylation, methylation or farnesylation. Accordingly, the present invention can include a peptide having an amino acid sequence substantially identical to that of a protein composed of the amino acid sequence represented by SEQ. ID. NO: 1 or SEQ. ID. NO: 2, and variants or fragments thereof. The substantially identical protein can have homology to the protein of the present invention by 80% or more, particularly 90% or more, and more particularly 95% or more.

The vector including the polynucleotide encoding the modified protein in which the 356$^{th}$ serine of Runx3 protein is substituted with an amino acid that cannot be phosphorylated by a kinase can be linear DNA or plasmid DNA.

The polynucleotide encoding the Runx3 protein can be composed of the amino acid sequence represented by SEQ. ID. NO: 3 or SEQ. ID. NO: 4.

The vector refers to a transport mediator for introducing the polynucleotide encoding the modified protein in which the 356$^{th}$ serine of Runx3 protein is substituted with an amino acid that cannot be phosphorylated by a kinase of the present invention into a subject to be treated, and can include a promoter suitable for expression in a subject to be treated, an enhancer, and a polynucleotide encoding the Runx3 protein, a transcription termination site, and the like. The promoter can be a specific organ and tissue specific promoter, and can include a replication origin so as to proliferate in the organ and tissue.

BRD2 (Bromodomain-containing protein 2) is a factor that acts as a signaling mediator in the nucleus. It is widely expressed in mammalian cells, and plays an important role in cell cycle regulation and transcriptional regulation.

The BRD2 binds to the acetylated Runx3.

The BRD2 is composed of BD1 and BD2.

The bromodomain 1 (BD1) of the BRD2 binds to the lysine residues 94 and 171 of Runx3.

The bromodomain 2 (BD2) of the BRD2 binds to the lysine residue 5 of the acetylated histone 4, the lysine residue 12 of histone 4, and the lysine residue 14 of histone 3.

When the complex is formed, cell death occurs.

In addition, the complex is formed upon receiving mitogenic stimulation.

The complex contributes to the determination of restriction point (R-point).

The virus transformed by the vector can be any one selected from the group consisting of retrovirus, adenovirus, herpes simplex virus and lentivirus, but not always limited thereto.

In the case of the vector containing the polynucleotide, it is preferably to contain 0.05 to 500 mg, and more preferably to contain 0.1 to 300 mg. In the case of the recombinant virus containing the polynucleotide encoding the modified protein in which the 356$^{th}$ serine of Runx3 protein is substituted with an amino acid that cannot be phosphorylated by a kinase, it is preferably to contain $10^3$ to $10^{12}$ IU (10 to $10^{10}$ PFU), and more preferably to contain $10^5$ to $10^{10}$ IU.

The recombinant virus is preferably adenovirus. Adeno-associated virus (AAV) is unsuitable as a delivery vehicle for cancer treatment because its gene expression rate or expression speed is lower than that of adenovirus. Adenovirus is suitable for the delivery of the modified protein according to the present invention to the human body because the transferred gene is expressed in adenovirus more than 3 weeks faster than in adeno-associated virus (HUMAN GENE THERAPY 15:405-413.), and the phenomenon of lowering the gene transfer efficiency due to the immune response is less in the adenovirus than in the adeno-associated virus (World J Gastroenterol. 2016 Jan. 7; 22(1):326-37).

The number of viruses for treatment can be represented by the number of viral particles including the vector genome or the number of infectable viruses. That is, since about 1% of the virus particles are the effective number of viruses that can actually be infected, IU (infection unit) or PFU (plaque forming unit) is used to indicate this.

The cell transformed by the vector can be bacterium.

The bacterium can be non-pathogenic or non-toxic, and can be *Listeria, Shigella, Salmonella*, or *E. coli*. By introducing the vector into bacteria, DNA of a gene included in the vector can be mass-replicated or proteins can be mass-produced.

The vector according to the present invention can be introduced into cells using a method known in the art. For example, transient transfection, microinjection, transduction, cell fusion, calcium phosphate precipitation, liposome-mediated transfection, DEAE dextran-mediated transfection, polybrene-mediated transfection, electroporation, gene gun, and other known methods for introducing nucleic acids into cells can be used to introduce the vector into cells, but not always limited thereto (Wu et al., J. Bio. Chem., 267: 963-967, 1992; Wu and Wu, J. Bio. Chem., 263:14621-14624, 1988).

In the case of the cells transformed with the vector containing the polynucleotide, it is preferably to contain $10^3$ to $10^8$ cells, and more preferably to contain $10^4$ to $10^7$ cells.

The pharmaceutical composition for prevention or treatment of cancer, comprising a modified protein in which the 356$^{th}$ serine of Runx3 (Runt-related transcription factor 3) is substituted with an amino acid that cannot be phosphorylated by a kinase, a polynucleotide coding thereof, a vector carrying the polynucleotide, or a virus or cell transformed with the vector as an active ingredient of the present invention can be administered parenterally during clinical administration.

The effective dose of the composition per 1 kg of body weight is 0.05 to 12.5 mg/kg for the vector, $10^7$ to $10^{11}$ virus particles ($10^5$ to $10^9$ IU)/kg for the recombinant virus, and $10^3$ to $10^6$ cells/kg for the cell. Preferably, the dose is 0.1 to 10 mg/kg for the vector, $10^8$ to $10^{10}$ virus particles ($10^6$ to $10^8$ IU)/kg for the recombinant virus, and $10^2$ to $10^5$ cells/kg for the cell. The composition can be administered 2 to 3 times a day. The composition as described above is not always limited thereto, and can vary depending on the conditions of a patient and the degree of onset of a disease.

The pharmaceutical composition according to the present invention may contain 10 to 95 weight % of a vector containing a Runx3 protein, a polynucleotide coding thereof, a vector carrying the polynucleotide, or a virus or cell transformed with the vector, which is an active ingredient, based on the total weight of the composition. In addition, the pharmaceutical composition of the present invention can include, in addition to the active ingredient, one or more effective ingredients having the same or similar function to the active ingredient.

Figure 3:
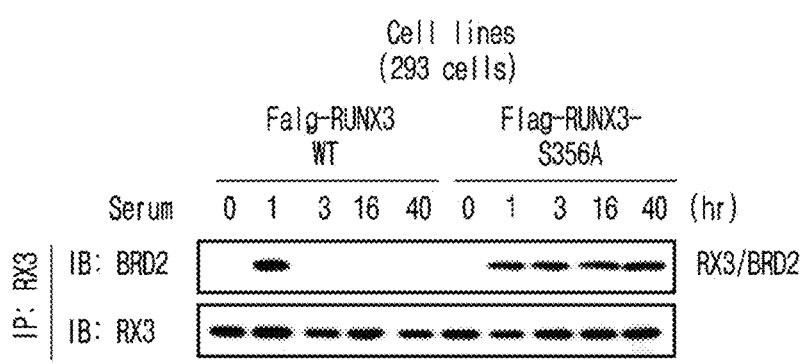
FIG. 3 is a diagram illustrating the time for the modified protein in which the 356$^{th}$ serine of Runx3 (Runt-related transcription factor 3) is substituted with an amino acid that cannot be phosphorylated by a kinase and the wild-type Runx3 protein forms a complex with Brd2 protein.
Figure 4A:
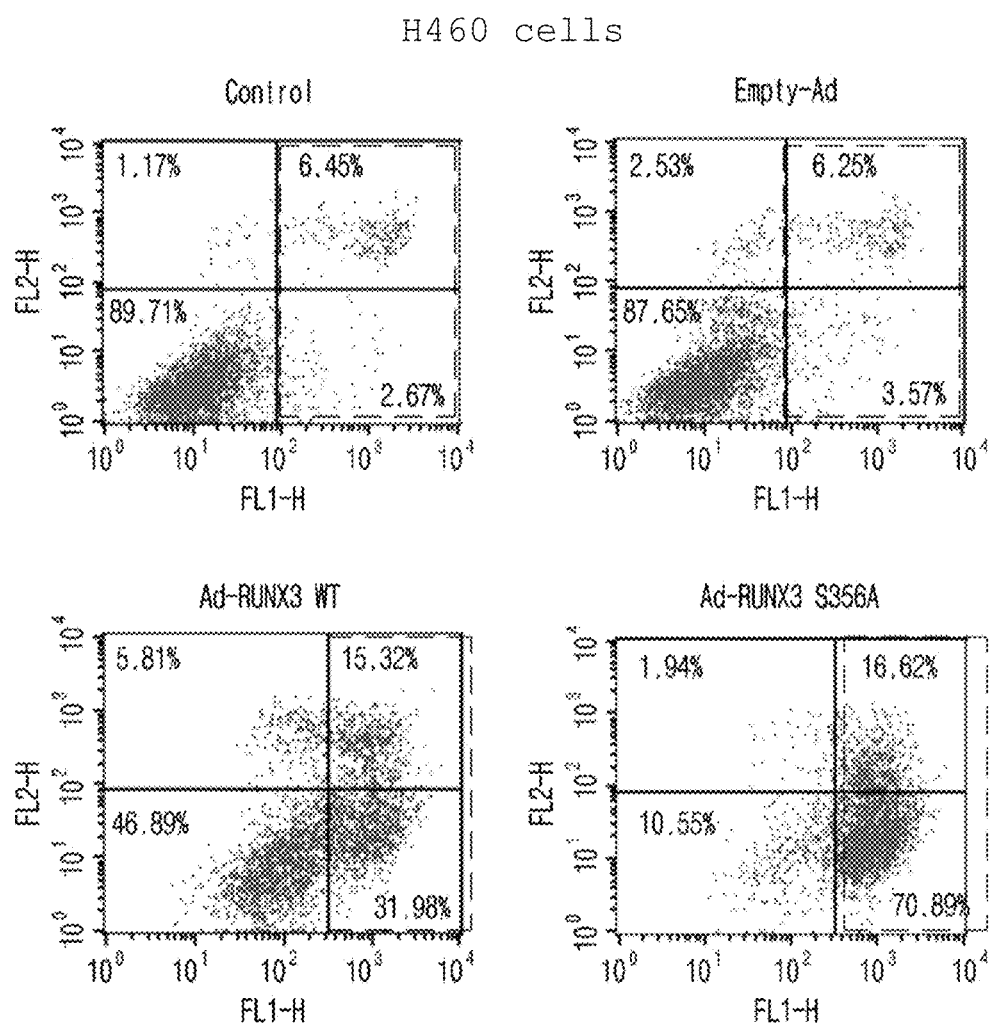
FIGS. 4a-c are diagrams illustrating the cancer cell death rates in lung cancer, stomach cancer, and pancreatic cancer cell lines when the modified protein in which the 356$^{th}$ serine of Runx3 (Runt-related transcription factor 3) is substituted with an amino acid that cannot be phosphorylated by a kinase and the wild-type Runx3 protein were administered.
Figure 4B:
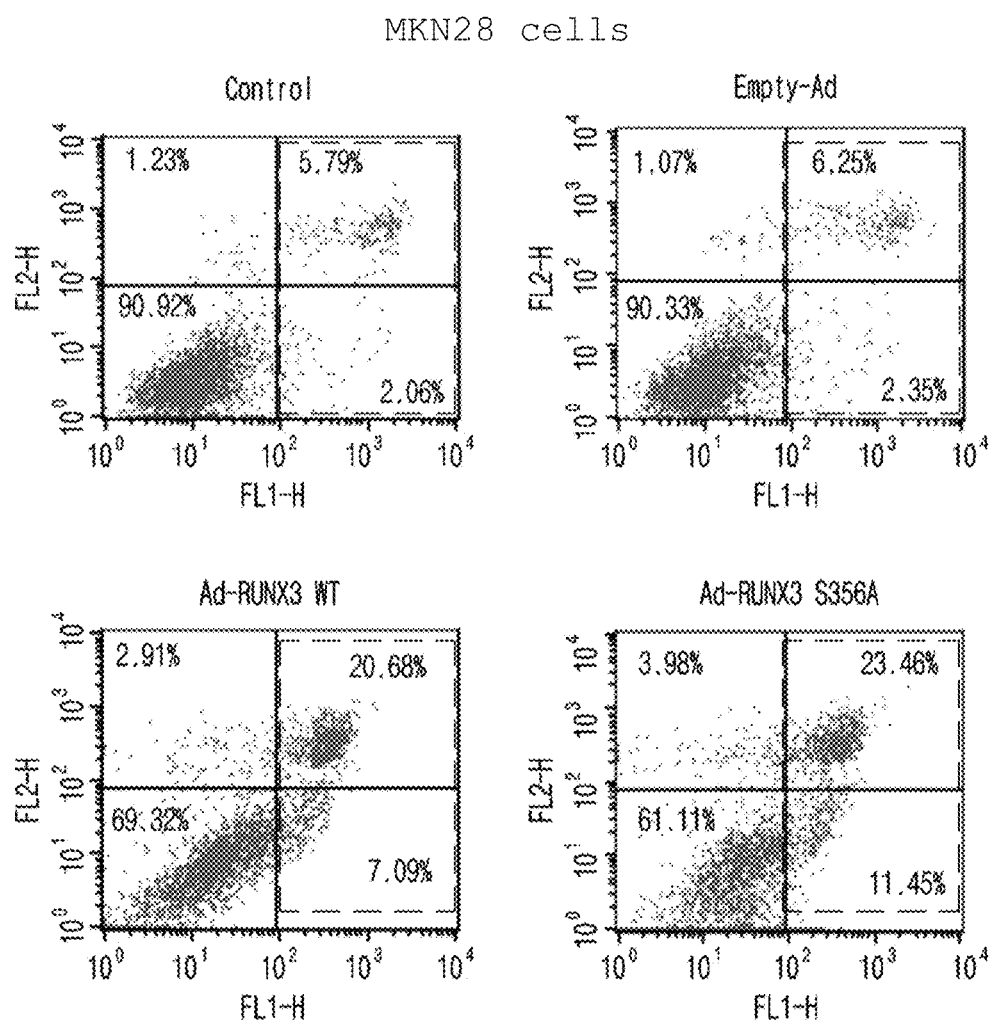
Figure 4C:
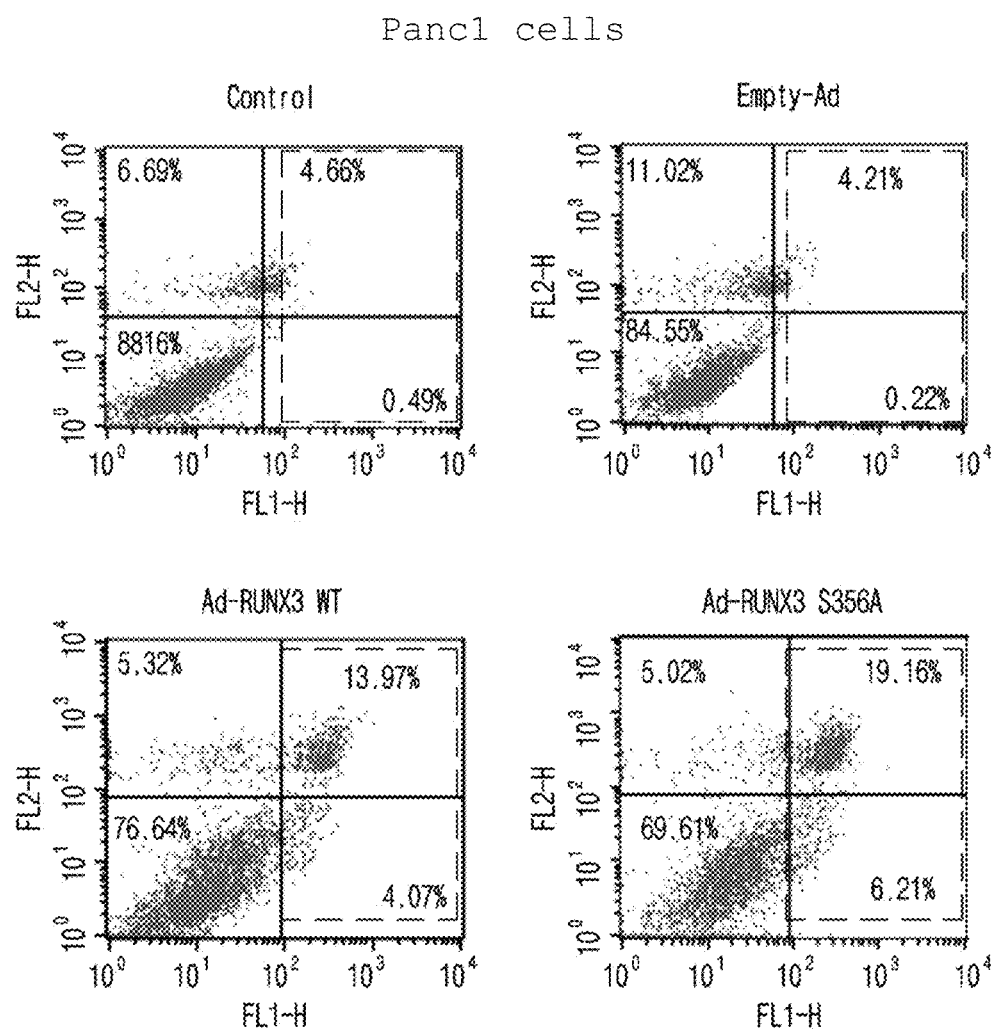

In preferred embodiments of the present invention, the present inventors confirmed that phosphorylation did not occur in the modified protein in which the 356$^{th}$ amino acid of Runx3 is substituted with another amino acid (FIGS. 2*a* to 2*j*), the modified protein had a complex maintenance activity of more than 10 times compared to that the binding between the wild-type Runx3 and BRD2 was separated after 3 hours since the physical binding of the modified protein in which the 356$^{th}$ serine of Runx3 is substituted with alanine with BRD2 was maintained for up to 40 hours (FIG. 3), and the modified protein in which the 356$^{th}$ serine of Runx3 is substituted with alanine was more effective in killing cancer cells in lung cancer, gastric cancer and pancreatic cancer cell lines compared to the wild-type Runx3 protein (FIGS. 4*a*-4*c* and 5).

Therefore, the modified protein in which the 356$^{th}$ serine of Runx3 (Runt-related transcription factor 3) is substituted with an amino acid that cannot be phosphorylated by a kinase, the polynucleotide coding thereof, the vector carrying the polynucleotide, or the virus or cell transformed with the vector can be used as a therapeutic agent for various cancers.

Hereinafter, the present invention will be described in detail by the following examples and experimental examples.

However, the following examples and experimental examples are only for illustrating the present invention, and the contents of the present invention are not limited thereto.

<Experimental Methods>

1. Cell Line Preparation

HEK293 cells (ATCC, Manassas, VA, USA) were maintained in DMEM medium (Gibco BRL, Thermo Fisher Scientific, MA, USA, MA) supplemented with 10% fetal bovine serum (Gibco BRL) and 1% penicillin/streptomycin (Invitrogen, Carlsbad, CA, USA).

H460 cells (ATCC, Manassas, VA, USA) and H460 stable cells were maintained in RPMI 1640 medium (Gibco BRL) supplemented with 10% fetal bovine serum (Gibco BRL) and 1% penicillin/streptomycin (Invitrogen). MKN28 cells (ATCC, Manassas, VA, USA) and PANC1 cells (ATCC, Manassas, VA, USA) were maintained in DMEM medium (Gibco BRL) supplemented with 10% fetal bovine serum (Gibco BRL) and penicillin/streptomycin (Invitrogen). All the cell lines were cultured in a 37° C., 5% $CO_2$ incubator.

2. Introduction of Runx3 and Runx3 S356A

Each cell line was cultured in a 10 cm culture dish ($5\times10^5$ cells) for 2 days and then approximately $2\times10^6$ cells of each cell line was infected with $1\times10^8$ VP of adenovirus or adenovirus Runx3 or adenovirus Runx3 S356A. After 48 hours, the cell death rate was measured by flow cytometry.

3. DNA Transfection, Immunoprecipitation (IP) and Immunoblotting (IB)

Transient transfection was performed in all cell lines using lipofectamine plus reagent and lipofectamine (Invitrogen). Cell lysates were incubated with an appropriate monoclonal or polyclonal antibody (2 μg of antibody/500 μg of lysate sample) at 4° C. for 3 hours, followed by incubation with protein G-Sepharose beads (Amersham Pharmacia Biotech, Piscataway, NJ, USA). For the detection of endogenous proteins at 4° C. for 1 hour, the lysate was incubated with an appropriate monoclonal or polyclonal antibody (1:1000~1:3000) at 4° C. for 6 to 12 hours, and then protein G-Sepharose beads (Amersham Pharmacia Biotech) were heated at 4° C. for 3 hours. The immune precipitate was digested on an SDS-polyacrylamide gel electrophoresis (SDS-PAGE) gel and transferred to a PVDF membrane (Millipore, Billerica, MA, USA). The membrane was blocked, immunoblotted with an appropriate antibody, treated with ECL solution (Amersham Pharmacia Biotech), and visualized in Amersham™ Imager 600 (GE Healthcare, Chicago, IL, USA).

4. Antibody

The antibody targeting RUNX3 (5G4) (Cat #ab40278) was obtained from Abcam (Cambridge, UK), and the antibody was diluted 1:3000. BRD2 (M01; 1:1000; Cat #H00006046-M01, Abnova, Taipei City, Taiwan) was used for immunoblotting and immunoprecipitation.

5. Flow Cytometry

Cells were harvested and processed using FITC-Annexin V Apoptosis Detection Kit I (BD Biosciences, San Jose, CA, USA) and propidium iodide DNA staining protocol. Apoptosis and cell cycle were analyzed by flow cytometry on a BD FACS caliber machine (BD Biosciences). All data were analyzed using FlowJo software (https://www.flowjo.com).

Example 1: Production of a Modified Protein in which the 356$^{th}$ Serine of Runx3 Protein is Substituted In the polynucleotide encoding the Runx3 protein registered in Genebank, mutant recombination was performed in the animal cell expression vector pCS4-3flag-RUNX3 using the primer sets listed in Table 1 including EcoRI-XhoI cleavage sites at both ends to induce mutations in the codon encoding the amino acid sequence of the 356$^{th}$ serine.

TABLE 1

| Name | Primer sequence | Characteristics |
|---|---|---|
| S356APrimer-F: (SEQ. ID. NO: 5) Primer-R: (SEQ. ID. NO: 6) Primer-M-F: (SEQ. ID. NO: 7) Primer-M-R: (SEQ. ID. NO: 8) | cgg gaa ttc a atg cgt att ccc gta att ctc gag tca gta ggg ccg c ggc gac cgc gca cct acc c g ggt agg tgc gcg gtc gcc | Serine was substituted with alanine. (TCA→GCA) |
| S356VPrimer-F: (SEQ. ID. NO: 9) Primer-R: (SEQ. ID. NO: 10) Primer-M-F: (SEQ. ID. NO: 11) Primer-M-R: (SEQ. ID. NO: 12) | cgg gaa ttc a atg cgt att ccc gta att ctc gag tca gta ggg ccg c ggc gac cgc gta cct acc c g ggt agg tac gcg gtc gcc | Serine was substituted with valine. (TCA→GTA) |
| S356IPrimer-F: (SEQ. ID. NO: 13) Primer-R: (SEQ. ID. NO: 14) Primer-M-F: (SEQ. ID. NO: 15) Primer-M-R: (SEQ. ID. NO: 16) | cgg gaa ttc a atg cgt att ccc gta att ctc gag tca gta ggg ccg c ggc gac cgc ata cct acc c g ggt agg tat gcg gtc gcc | Serine was substituted with isoleucine. (TCA→ATA) |
| S356LPrimer-F: (SEQ. ID. NO: 17) Primer-R: | cgg gaa ttc a atg cgt att ccc gta att ctc gag tca gta ggg ccg c | Serine was substituted with leucine. |

TABLE 1-continued

| Name Primer sequence | Characteristics |
|---|---|
| (SEQ. ID. NO: 18)<br>Primer-M-F: ggc gac cgc cta cct acc c<br>(SEQ. ID. NO: 19)<br>Primer-M-R: g ggt agg tag gcg gtc gcc<br>(SEQ. ID. NO: 20) | (TCA→CTA) |
| S356GPrimer-F: cgg gaa ttc a atg cgt att ccc gta<br>(SEQ. ID. NO: 21)<br>Primer-R: att ctc gag tca gta ggg ccg c<br>(SEQ. ID. NO: 22)<br>Primer-M-F: ggc gac cgc gga cct acc c<br>(SEQ. ID. NO: 23)<br>Primer-M-R: g ggt agg tcc gcg gtc gcc<br>(SEQ. ID. NO: 24) | Serine was substituted with glycine.<br>(TCA→GGA) |
| S356RPrimer-F: cgg gaa ttc a atg cgt att ccc gta<br>(SEQ. ID. NO: 25)<br>Primer-R: att ctc gag tca gta ggg ccg c<br>(SEQ. ID. NO: 26)<br>Primer-M-F: ggc gac cgc cga cct acc c<br>(SEQ. ID. NO: 27)<br>Primer-M-R: g ggt agg tcg gcg gtc gcc<br>(SEQ. ID. NO: 28) | Serine was substituted with arginine.<br>(TCA→CGA) |
| S356NPrimer-F: cgg gaa ttc a atg cgt att ccc gta<br>(SEQ. ID. NO: 29)<br>Primer-R: att ctc gag tca gta ggg ccg c<br>(SEQ. ID. NO: 30)<br>Primer-M-F: ggc gac cgc aat cct acc c<br>(SEQ. ID. NO: 31)<br>Primer-M-R: g ggt agg att gcg gtc gcc<br>(SEQ. ID. NO: 32) | Serine was substituted with asparagine.<br>(TCA→AAT) |
| S356CPrimer-F: cgg gaa ttc a atg cgt att ccc gta<br>(SEQ. ID. NO: 33)<br>Primer-R: att ctc gag tca gta ggg ccg c<br>(SEQ. ID. NO: 34)<br>Primer-M-F: ggc gac cgc tgc cct acc c<br>(SEQ. ID. NO: 35)<br>Primer-M-R: g ggt agg gca gcg gtc gcc<br>(SEQ. ID. NO: 36) | Serine was substituted with cysteine.<br>(TCA→TGC) |
| S356QPrimer-F: cgg gaa ttc a atg cgt att ccc gta<br>(SEQ. ID. NO: 37)<br>Primer-R: att ctc gag tca gta ggg ccg c<br>(SEQ. ID. NO: 38)<br>Primer-M-F: ggc gac cgc caa cct acc c<br>(SEQ. ID. NO: 39)<br>Primer-M-R: g ggt agg ttg gcg gtc gcc<br>(SEQ. ID. NO: 40) | Serine was substituted with glutamine.<br>(TCA→CAA) |
| S356HPrimer-F: cgg gaa ttc a atg cgt att ccc gta<br>(SEQ. ID. NO: 41)<br>Primer-R: att ctc gag tca gta ggg ccg c<br>(SEQ. ID. NO: 42)<br>Primer-M-F: ggc gac cgc cac cct acc c<br>(SEQ. ID. NO: 43)<br>Primer-M-R: g ggt agg gtg gcg gtc gcc<br>(SEQ. ID. NO: 44) | Serine was substituted with histidine.<br>(TCA→CAC) |
| S356KPrimer-F: cgg gaa ttc a atg cgt att ccc gta<br>(SEQ. ID. NO: 45)<br>Primer-R: att ctc gag tca gta ggg ccg c<br>(SEQ. ID. NO: 46)<br>Primer-M-F: ggc gac cgc aaa cct acc c<br>(SEQ. ID. NO: 47)<br>Primer-M-R: g ggt agg ttt gcg gtc gcc<br>(SEQ. ID. NO: 48) | Serine was substituted with lysine.<br>(TCA→AAA) |
| S356MPrimer-F: cgg gaa ttc a atg cgt att ccc gta<br>(SEQ. ID. NO: 49)<br>Primer-R: att ctc gag tca gta ggg ccg c<br>(SEQ. ID. NO: 50)<br>Primer-M-F: ggc gac cgc atg cct acc c<br>(SEQ. ID. NO: 51)<br>Primer-M-R: g ggt agg cat gcg gtc gcc<br>(SEQ. ID. NO: 52) | Serine was substituted with methionine.<br>(TCA→ATG) |

TABLE 1-continued

| Name | Primer sequence | Characteristics |
|---|---|---|
| S356FPrimer-F:<br>(SEQ. ID. NO: 53)<br>Primer-R:<br>(SEQ. ID. NO: 54)<br>Primer-M-F:<br>(SEQ. ID. NO: 55)<br>Primer-M-R:<br>(SEQ. ID. NO: 56) | cgg gaa ttc a atg cgt att ccc gta<br><br>att ctc gag tca gta ggg ccg c<br><br>ggc gac cgc ttc cct acc c<br><br>g ggt agg gaa gcg gtc gcc | Serine was substituted with phenylalanine. (TCA→TTC) |
| S356PPrimer-F:<br>(SEQ. ID. NO: 57)<br>Primer-R:<br>(SEQ. ID. NO: 58)<br>Primer-M-F:<br>(SEQ. ID. NO: 59)<br>Primer-M-R:<br>(SEQ. ID. NO: 60) | cgg gaa ttc a atg cgt att ccc gta<br><br>att ctc gag tca gta ggg ccg c<br><br>ggc gac cgc cca cct acc c<br><br>g ggt agg tgg gcg gtc gcc | Serine was substituted with proline. (TCA→CCA) |
| S356WPrimer-F:<br>(SEQ. ID. NO: 61)<br>Primer-R:<br>(SEQ. ID. NO: 62)<br>Primer-M-F:<br>(SEQ. ID. NO: 63)<br>Primer-M-R:<br>(SEQ. ID. NO: 64) | cgg gaa ttc a atg cgt att ccc gta<br><br>att ctc gag tca gta ggg ccg c<br><br>ggc gac cgc tgg cct acc c<br><br>g ggt agg cca gcg gtc gcc | Serine was substituted with tryptophane. (TCA→TGG) |

Particularly, pCS4-flag-RUNX3 plasmid was digested with EcoRI/XhoI restriction enzyme and polymerase chain reaction (PCR) was performed with each Primer-F/Primer-M-R (Resulting Insert: F) and Primer-M-F/Primer-R (Resulting Insert: R) using RUNX3 Insert as a template. The PCR product was purified, and the secondary polymerase chain reaction was performed with F and R templates, Primer-F and Primer-R. The RUNX3 S356A PCR product obtained by the secondary polymerase chain reaction was purified. RUNX3 S356A and pCS4-flag-Vector were digested with EcoRI/XhoI restriction enzyme, gel-extracted, ligated, and transfected. Only single colony was cultured in 2 ml and of LB medium, and the cloned plasmid was separated and purified to confirm the nucleotide sequence.

Experimental Example 1: Confirmation of Phosphorylation Inhibitory Effect when the 356$^{th}$ Serine of Runx3 Protein is Substituted RUNX3 phosphorylation in serine, the 356$^{th}$ amino acid of Runx3 protein, was measured by immunoprecipitation (IP) and immunoblotting (IB) in the same manner as described in Experimental Method 3 above.

As a result, as shown in FIG. 1, the binding between Myc-RUNX3-S356A and BRD2 was maintained until 8 hours after the serum stimulation. The above results indicate that substitution of serine, the 356$^{th}$ amino acid of Runx3 protein, to alanine inhibited phosphorylation of Runx3, thereby the time for maintaining the binding with BRD2 was increased.

Experimental Example 2: Confirmation of Non-Phosphorylation of 356$^{th}$ Amino Acid of Runx3 Modified Protein The possibility of phosphorylation of the 356$^{th}$ amino acid of the prepared mutant was verified using a phosphorylation level prediction tool (Phospho.elm:http://phospho.elm.eu.org/pELMB lastSearch.html) and NETPhos 3.1 (cbs.dtu.dk/services/NetPhos/). As a result, as shown in Table 2 and FIGS. 2a to 2j, it was confirmed that there was no phosphorylation in the part.

The above results indicate that when the 356$^{th}$ amino acid of Runx3 was substituted with another amino acid, the phosphorylation of Runx3 was suppressed, and thus the time for maintaining the binding with BRD2 was increased.

TABLE 2

| | 356$^{th}$ amino acid | Phosphorylation prediction result |
|---|---|---|
| S356 wild type | Serine | O |
| S356A | Alanine | X |
| S356I | Isoleucine | X |
| S356L | Leucine | X |
| S356V | Valine | X |
| S356C | Cysteine | X |
| S356F | Phenylalanine | X |
| S356G | Glycine | X |
| S356K | Lysine | X |
| S356H | Histidine | X |
| S356M | Methionine | X |
| S356N | asparagine | X |
| S356P | Proline | X |
| S356Q | Glutamine | X |
| S356R | arginine | X |
| S356W | tryptophan | X |

Experimental Example 3: Confirmation of Increasing Effect on the Stability of Runx3 Protein by Runx3 S356A Modified Protein The modified protein in which the 356$^{th}$ amino acid of Runx3 is substituted with alanine blocks the physical binding between Runx3 and CDK4, thereby inhibiting the phosphorylation of the 356$^{th}$ serine of Runx3 by CDK4. By inhibiting the conversion of the Rpa-Rx3-AC complex including Runx3 to the Rpa-Rx3-TR complex, the function of maintaining the anticancer activity of Runx3 is improved. Thus, the following experiment was performed to compare the time for the modified protein in which the 356$^{th}$ amino acid of Runx3 is substituted with alanine to form a complex by binding to Brd2 protein with the wild-type Runx3.

Particularly, the antibody targeting RUNX3 (5G4) (Cat #ab40278) was obtained from Abcam (Cambridge, UK), and the antibody was diluted 1:3000. BRD2 (M01; 1:1000; Cat #H00006046-M01, Abnova, Taipei City, Taiwan) was used for immunoblotting and immunoprecipitation. Transient transfection was performed in all cell lines using lipofectamine plus reagent and lipofectamine (Invitrogen). Cell lysates were incubated with an appropriate monoclonal or polyclonal antibody (2 μg of antibody/500 μg of lysate sample) at 4° C. for 3 hours, followed by incubation with protein G-Sepharose beads (Amersham Pharmacia Biotech, Piscataway, N.J., USA). For the detection of endogenous proteins at 4° C. for 1 hour, the lysate was incubated with an appropriate monoclonal or polyclonal antibody (1:1000~1:3000) at 4° C. for 6 to 12 hours, and then protein G-Sepharose beads (Amersham Pharmacia Biotech) were heated at 4° C. for 3 hours. The immune precipitate was digested on SDS-polyacrylamide gel electrophoresis (SDS-PAGE) gel and transferred to a PVDF membrane (Millipore, Billerica, MA, USA). The membrane was blocked, immunoblotted with an appropriate antibody, treated with ECL solution (Amersham Pharmacia Biotech), and visualized in Amersham™ Imager 600 (GE Healthcare, Chicago, IL, USA).

As a result, as shown in FIGS. 2a-2j, the wild-type Runx3 bound with Brd2 and formed a complex for up to 8 hours, but the modified protein in which the 356$^{th}$ serine of Runx3 is substituted with alanine maintained the physical binding with BRD2 for up to 40 hours. Thus, it was confirmed that the modified protein had a complex maintenance activity of 10 times or more compared to the wild-type, as the binding of the wild-type Runx3 and BRD2 was separated from 3 hours after the binding.

Experimental Example 4: Confirmation of Apoptotic Effect of Runx3 S356A Modified Protein More Effective than Wild-Type Runx3 on Solid Cancer Cell Lines It was confirmed through flow cytometry that the Runx3 S356A modified protein improved the maintenance efficacy of the Runx3-Brd2 complex, and the apoptosis ability thereof was improved in various cancer cell lines compared to the wild-type Runx3.

Particularly, each cell line prepared according to Experimental Method 1 above was harvested and processed using FITC-Annexin V Apoptosis Detection Kit I (BD Biosciences, San Jose, Calif., USA) and propidium iodide DNA staining protocol. Apoptosis and cell cycle were analyzed by flow cytometry on a BD FACS caliber machine (BD Biosciences). All data were analyzed using FlowJo software (https://www.flowjo.com).

As a result, as shown in FIGS. 3 and 4a-4c, the modified protein in which the 356$^{th}$ serine of Runx3 is substituted with alanine increased the apoptosis rate by about 2 times or more in lung cancer cell lines, and further increased the cancer cell death efficacy in stomach cancer and pancreatic cancer cell lines compared to the wild-type Runx3 protein.

Experimental Example 5: Measurement of Runx3 Expression Level in Runx3 S356A Modified Protein and Wild-Type Runx3 Protein Western blotting was performed as described in Experimental Method 3 to confirm the expression of Runx3 protein in adenovirus expressing the Runx3 S356A modified protein and the wild-type Runx3.

Figure 5:
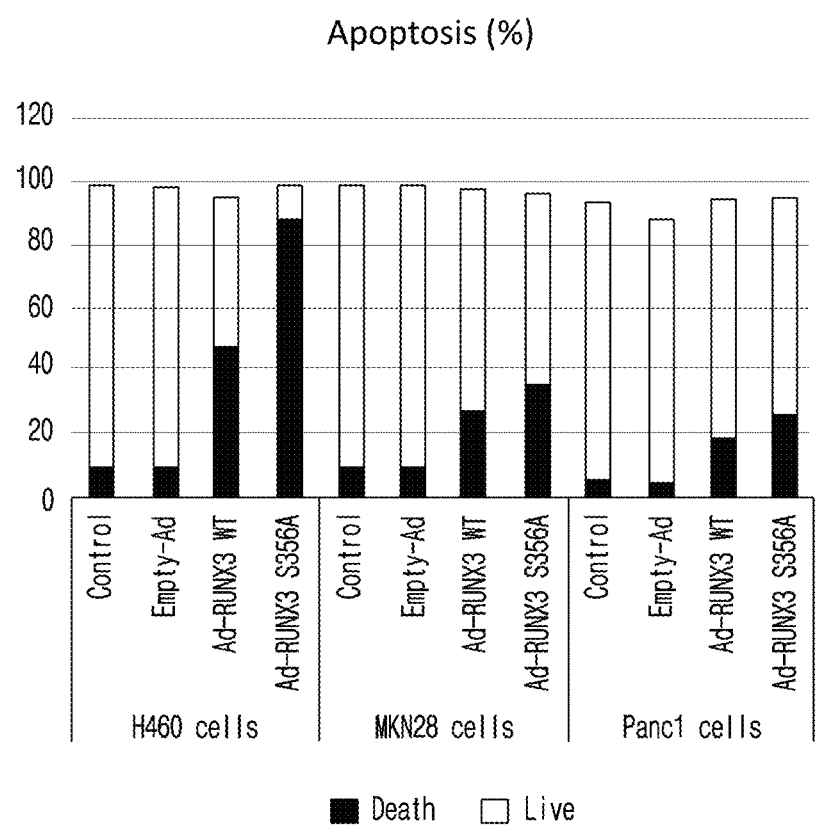
FIG. 5 is a diagram illustrating the percentage of cells killed in the lung cancer cell line and the stomach cancer cell line when the modified protein in which the 356$^{th}$ serine of Runx3 (Runt-related transcription factor 3) is substituted with an amino acid that cannot be phosphorylated by a kinase and the wild-type Runx3 protein were administered, confirmed by flow cytometry.
Figure 6:
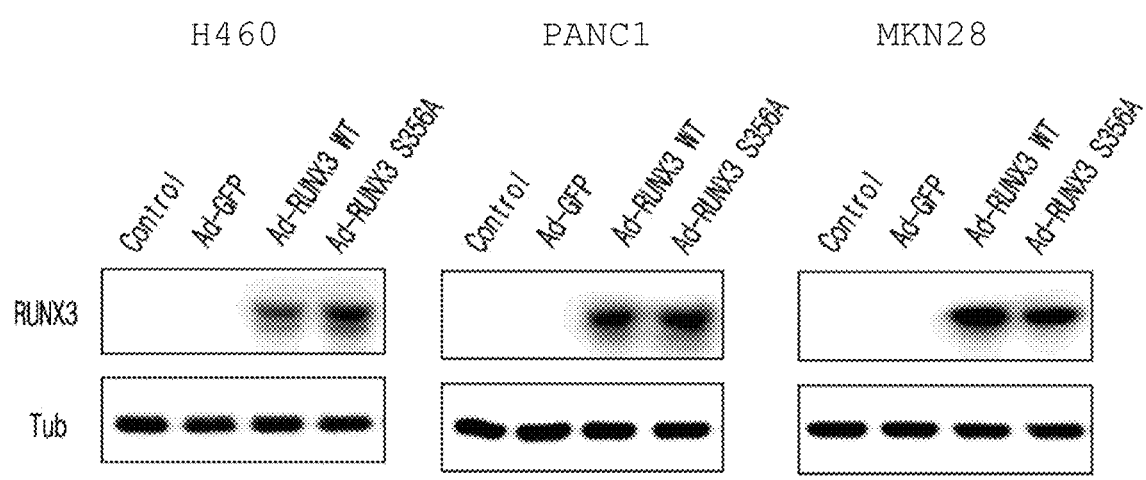
FIG. 6 is a diagram confirming the expression of Runx3 protein in the adenovirus introduced with the polynucleotide coding the Runx3 S356A modified protein and the wild-type Runx3 protein.

As a result, as shown in FIG. 5, it was confirmed that the Runx3 protein was expressed in both the adenovirus into which the polynucleotide encoding the Runx3 S356A modified protein was introduced and the adenovirus into which the polynucleotide encoding the wild-type Runx3 protein was introduced.

SEQUENCE LISTING

```
<160> NUMBER OF SEQ ID NOS: 64

<210> SEQ ID NO 1
<211> LENGTH: 429
<212> TYPE: PRT
<213> ORGANISM: Artificial Sequence
<220> FEATURE:
<223> OTHER INFORMATION: Runx3 isoform1 amino acid

<400> SEQUENCE: 1

Met Ala Ser Asn Ser Ile Phe Asp Ser Phe Pro Thr Tyr Ser Pro Thr
1               5                   10                  15

Phe Ile Arg Asp Pro Ser Thr Ser Arg Arg Phe Thr Pro Pro Ser Pro
            20                  25                  30

Ala Phe Pro Cys Gly Gly Gly Gly Lys Met Gly Glu Asn Ser Gly
        35                  40                  45

Ala Leu Ser Ala Gln Ala Ala Val Gly Pro Gly Gly Arg Ala Arg Pro
    50                  55                  60

Glu Val Arg Ser Met Val Asp Val Leu Ala Asp His Ala Gly Glu Leu
65                  70                  75                  80

Val Arg Thr Asp Ser Pro Asn Phe Leu Cys Ser Val Leu Pro Ser His
                85                  90                  95

Trp Arg Cys Asn Lys Thr Leu Pro Val Ala Phe Lys Val Val Ala Leu
```

```
                    100                 105                 110
Gly Asp Val Pro Asp Gly Thr Val Thr Val Met Ala Gly Asn Asp
            115                 120                 125

Glu Asn Tyr Ser Ala Glu Leu Arg Asn Ala Ser Ala Val Met Lys Asn
        130                 135                 140

Gln Val Ala Arg Phe Asn Asp Leu Arg Phe Val Gly Arg Ser Gly Arg
145                 150                 155                 160

Gly Lys Ser Phe Thr Leu Thr Ile Thr Val Phe Thr Asn Pro Thr Gln
                165                 170                 175

Val Ala Thr Tyr His Arg Ala Ile Lys Val Thr Val Asp Gly Pro Arg
            180                 185                 190

Glu Pro Arg Arg His Arg Gln Lys Leu Glu Asp Gln Thr Lys Pro Phe
        195                 200                 205

Pro Asp Arg Phe Gly Asp Leu Glu Arg Leu Arg Met Arg Val Thr Pro
    210                 215                 220

Ser Thr Pro Ser Pro Arg Gly Ser Leu Ser Thr Thr Ser His Phe Ser
225                 230                 235                 240

Ser Gln Pro Gln Thr Pro Ile Gln Gly Thr Ser Glu Leu Asn Pro Phe
                245                 250                 255

Ser Asp Pro Arg Gln Phe Asp Arg Ser Phe Pro Thr Leu Pro Thr Leu
            260                 265                 270

Thr Glu Ser Arg Phe Pro Asp Pro Arg Met His Tyr Pro Gly Ala Met
        275                 280                 285

Ser Ala Ala Phe Pro Tyr Ser Ala Thr Pro Ser Gly Thr Ser Ile Ser
    290                 295                 300

Ser Leu Ser Val Ala Gly Met Pro Ala Thr Ser Arg Phe His His Thr
305                 310                 315                 320

Tyr Leu Pro Pro Pro Tyr Pro Gly Ala Pro Gln Asn Gln Ser Gly Pro
                325                 330                 335

Phe Gln Ala Asn Pro Ser Pro Tyr His Leu Tyr Tyr Gly Thr Ser Ser
            340                 345                 350

Gly Ser Tyr Gln Phe Ser Met Val Ala Gly Ser Ser Gly Gly Asp
        355                 360                 365

Arg Ser Pro Thr Arg Met Leu Ala Ser Cys Thr Ser Ser Ala Ala Ser
    370                 375                 380

Val Ala Ala Gly Asn Leu Met Asn Pro Ser Leu Gly Gly Gln Ser Asp
385                 390                 395                 400

Gly Val Glu Ala Asp Gly Ser His Ser Asn Ser Pro Thr Ala Leu Ser
                405                 410                 415

Thr Pro Gly Arg Met Asp Glu Ala Val Trp Arg Pro Tyr
            420                 425

<210> SEQ ID NO 2
<211> LENGTH: 415
<212> TYPE: PRT
<213> ORGANISM: Artificial Sequence
<220> FEATURE:
<223> OTHER INFORMATION: Runx3 isoform2 amino acid

<400> SEQUENCE: 2

Met Arg Ile Pro Val Asp Pro Ser Thr Ser Arg Arg Phe Thr Pro Pro
1               5                   10                  15

Ser Pro Ala Phe Pro Cys Gly Gly Gly Gly Lys Met Gly Glu Asn
            20                  25                  30

Ser Gly Ala Leu Ser Ala Gln Ala Ala Val Gly Pro Gly Gly Arg Ala
```

```
              35                  40                  45
Arg Pro Glu Val Arg Ser Met Val Asp Val Leu Ala Asp His Ala Gly
 50                  55                  60

Glu Leu Val Arg Thr Asp Ser Pro Asn Phe Leu Cys Ser Val Leu Pro
 65                  70                  75                  80

Ser His Trp Arg Cys Asn Lys Thr Leu Pro Val Ala Phe Lys Val Val
                     85                  90                  95

Ala Leu Gly Asp Val Pro Asp Gly Thr Val Val Thr Val Met Ala Gly
                100                 105                 110

Asn Asp Glu Asn Tyr Ser Ala Glu Leu Arg Asn Ala Ser Ala Val Met
                115                 120                 125

Lys Asn Gln Val Ala Arg Phe Asn Asp Leu Arg Phe Val Gly Arg Ser
130                 135                 140

Gly Arg Gly Lys Ser Phe Thr Leu Thr Ile Thr Val Phe Thr Asn Pro
145                 150                 155                 160

Thr Gln Val Ala Thr Tyr His Arg Ala Ile Lys Val Thr Val Asp Gly
                165                 170                 175

Pro Arg Glu Pro Arg Arg His Arg Gln Lys Leu Glu Asp Gln Thr Lys
                180                 185                 190

Pro Phe Pro Asp Arg Phe Gly Asp Leu Glu Arg Leu Arg Met Arg Val
                195                 200                 205

Thr Pro Ser Thr Pro Ser Pro Arg Gly Ser Leu Ser Thr Thr Ser His
210                 215                 220

Phe Ser Ser Gln Pro Gln Thr Pro Ile Gln Gly Thr Ser Glu Leu Asn
225                 230                 235                 240

Pro Phe Ser Asp Pro Arg Gln Phe Asp Arg Ser Phe Pro Thr Leu Pro
                245                 250                 255

Thr Leu Thr Glu Ser Arg Phe Pro Asp Pro Arg Met His Tyr Pro Gly
                260                 265                 270

Ala Met Ser Ala Ala Phe Pro Tyr Ser Ala Thr Pro Ser Gly Thr Ser
                275                 280                 285

Ile Ser Ser Leu Ser Val Ala Gly Met Pro Ala Thr Ser Arg Phe His
290                 295                 300

His Thr Tyr Leu Pro Pro Pro Tyr Pro Gly Ala Pro Gln Asn Gln Ser
305                 310                 315                 320

Gly Pro Phe Gln Ala Asn Pro Ser Pro Tyr His Leu Tyr Tyr Gly Thr
                325                 330                 335

Ser Ser Gly Ser Tyr Gln Phe Ser Met Val Ala Gly Ser Ser Ser Gly
                340                 345                 350

Gly Asp Arg Ser Pro Thr Arg Met Leu Ala Ser Cys Thr Ser Ser Ala
                355                 360                 365

Ala Ser Val Ala Ala Gly Asn Leu Met Asn Pro Ser Leu Gly Gly Gln
                370                 375                 380

Ser Asp Gly Val Glu Ala Asp Gly Ser His Ser Asn Ser Pro Thr Ala
385                 390                 395                 400

Leu Ser Thr Pro Gly Arg Met Asp Glu Ala Val Trp Arg Pro Tyr
                405                 410                 415

<210> SEQ ID NO 3
<211> LENGTH: 1380
<212> TYPE: DNA
<213> ORGANISM: Artificial Sequence
<220> FEATURE:
<223> OTHER INFORMATION: Runx3 isoform1 polynucleotide
```

<400> SEQUENCE: 3

```
gccttcttca gagcggggca tggcatcgaa cagcatcttc gactccttcc cgacctactc    60
gccgaccttc atccgcgacc caagcaccag ccgccgcttc acacctccct ccccggcctt   120
cccctgcggc ggcggcggcg gcaagatggg cgagaacagc ggcgcgctga gcgcgcaggc   180
ggccgtgggg cccggagggc gcgcccggcc cgaggtgcgc tcgatggtgg acgtgctggc   240
ggaccacgca ggcgagctcg tgcgcaccga cagccccaac ttcctctgct ccgtgctgcc   300
ctcgcactgg cgctgcaaca agacgctgcc cgtcgccttc aaggtggtgg cattgggggga  360
cgtgccggat ggtacggtgg tgactgtgat ggcaggcaat gacgagaact actccgctga   420
gctgcgcaat gcctcggccg tcatgaagaa ccaggtggcc aggttcaacg accttcgctt   480
cgtgggccgc agtgggcgag ggaagagttt caccctgacc atcactgtgt tcaccaaccc   540
cacccaagtg gcgacctacc accgagccat caaggtgacc gtggacggac cccgggagcc   600
cagacggcac cggcagaagc tggaggacca gaccaagccg ttccctgacc gctttgggga   660
cctggaacgg ctgcgcatgc gggtgacacc gagcacaccc agccccgag gctcactcag    720
caccacaagc cacttcagca gccagcccca gaccccaatc caaggcacct cggaactgaa   780
cccattctcc gaccccgcc agtttgaccg ctccttcccc acgctgccaa ccctcacgga    840
gagccgcttc ccagaccca ggatgcatta tcccggggcc atgtcagctg ccttcccta    900
cagccgacacg ccctcgggca cgagcatcag cagcctcagc gtggcgggca tgccggccac  960
cagccgcttc caccatacct acctcccgcc accctaccg ggggccccgc agaaccagag   1020
cgggcccttc caggccaacc cgtcccccta ccacctctac tacgggacat cctctggctc   1080
ctaccagttc tccatggtgg ccggcagcag cagtgggggc gaccgctcac ctacccgcat   1140
gctgcctct tgcaccagca gcgctgcctc tgtcgccgcc ggcaacctca tgaacccag    1200
cctgggcggc cagagtgatg gcgtggaggc cgacggcagc cacagcaact cacccacggc   1260
cctgagcacg ccaggccgca tggatgaggc cgtgtggcgg ccctactgac cgccctggtg   1320
gactcctccc gctggaggcg gggaccctaa caaccttcaa gaccagtgat gggccggctc   1380
```

<210> SEQ ID NO 4
<211> LENGTH: 1320
<212> TYPE: DNA
<213> ORGANISM: Artificial Sequence
<220> FEATURE:
<223> OTHER INFORMATION: Run3 isoform2 polynucleotide

<400> SEQUENCE: 4

```
cgggggaagc cgcgccgtct ccgcctgccc ggcgccctga cggccgctgt tatgcgtatt    60
cccgtagacc caagcaccag ccgccgcttc acacctccct ccccggcctt cccctgcggc   120
ggcggcggcg gcaagatggg cgagaacagc ggcgcgctga gcgcgcaggc ggccgtgggg   180
cccggagggc gcgcccggcc cgaggtgcgc tcgatggtgg acgtgctggc ggaccacgca   240
ggcgagctcg tgcgcaccga cagccccaac ttcctctgct ccgtgctgcc ctcgcactgg   300
cgctgcaaca agacgctgcc cgtcgccttc aaggtggtgg cattgggggga cgtgccggat   360
ggtacggtgg tgactgtgat ggcaggcaat gacgagaact actccgctga gctgcgcaat   420
gcctcggccg tcatgaagaa ccaggtggcc aggttcaacg accttcgctt cgtgggccgc   480
agtgggcgag ggaagagttt caccctgacc atcactgtgt tcaccaaccc cacccaagtg   540
gcgacctacc accgagccat caaggtgacc gtggacggac cccgggagcc cagacggcac   600
cggcagaagc tggaggacca gaccaagccg ttccctgacc gctttgggga cctggaacgg   660
```

```
ctgcgcatgc gggtgacacc gagcacaccc agcccccgag gctcactcag caccacaagc    720
cacttcagca gccagcccca gaccccaatc caaggcacct cggaactgaa cccattctcc    780
gacccccgcc agtttgaccg ctccttcccc acgctgccaa ccctcacgga gagccgcttc    840
ccagacccca ggatgcatta tcccggggcc atgtcagctg ccttcccta cagcgccacg     900 ccctcgggca cgagcatcag cagcctcagc gtggcgggca tgccggccac cagccgcttc    960
caccatacct acctcccgcc accctacccg ggggccccgc agaaccagag cgggcccttc   1020
caggccaacc cgtcccccta ccacctctac tacgggacat cctctggctc ctaccagttc   1080
tccatggtgg ccggcagcag cagtgggggc gaccgctcac ctacccgcat gctggcctct   1140
tgcaccagca gcgctgcctc tgtcgccgcc ggcaacctca tgaacccag cctgggcggc    1200 cagagtgatg gcgtggaggc cgacggcagc cacagcaact cacccacggc cctgagcacg   1260
ccaggccgca tggatgaggc cgtgtggcgg ccctactgac cgccctggtg gactcctccc   1320

<210> SEQ ID NO 5
<211> LENGTH: 25
<212> TYPE: DNA
<213> ORGANISM: Artificial Sequence
<220> FEATURE:
<223> OTHER INFORMATION: S356A Primer-F

<400> SEQUENCE: 5
cgggaattca atgcgtattc ccgta                                           25

<210> SEQ ID NO 6
<211> LENGTH: 22
<212> TYPE: DNA
<213> ORGANISM: Artificial Sequence
<220> FEATURE:
<223> OTHER INFORMATION: S356A Primer-R

<400> SEQUENCE: 6
attctcgagt cagtagggcc gc                                              22

<210> SEQ ID NO 7
<211> LENGTH: 19
<212> TYPE: DNA
<213> ORGANISM: Artificial Sequence
<220> FEATURE:
<223> OTHER INFORMATION: S356A Primer-M-F

<400> SEQUENCE: 7
ggcgaccgcg cacctaccc                                                  19

<210> SEQ ID NO 8
<211> LENGTH: 19
<212> TYPE: DNA
<213> ORGANISM: Artificial Sequence
<220> FEATURE:
<223> OTHER INFORMATION: S356A Primer-M-R

<400> SEQUENCE: 8
gggtaggtgc gcggtcgcc                                                  19

<210> SEQ ID NO 9
<211> LENGTH: 25
<212> TYPE: DNA
<213> ORGANISM: Artificial Sequence
<220> FEATURE:
<223> OTHER INFORMATION: S356V Primer-F
```

```
<400> SEQUENCE: 9
cgggaattca atgcgtattc ccgta                                    25

<210> SEQ ID NO 10
<211> LENGTH: 22
<212> TYPE: DNA
<213> ORGANISM: Artificial Sequence
<220> FEATURE:
<223> OTHER INFORMATION: S356V Primer-R

<400> SEQUENCE: 10
attctcgagt cagtagggcc gc                                       22

<210> SEQ ID NO 11
<211> LENGTH: 19
<212> TYPE: DNA
<213> ORGANISM: Artificial Sequence
<220> FEATURE:
<223> OTHER INFORMATION: S356V Primer-M-F

<400> SEQUENCE: 11
ggcgaccgcg tacctaccc                                           19

<210> SEQ ID NO 12
<211> LENGTH: 19
<212> TYPE: DNA
<213> ORGANISM: Artificial Sequence
<220> FEATURE:
<223> OTHER INFORMATION: S356V Primer-M-R

<400> SEQUENCE: 12
gggtaggtac gcggtcgcc                                           19

<210> SEQ ID NO 13
<211> LENGTH: 25
<212> TYPE: DNA
<213> ORGANISM: Artificial Sequence
<220> FEATURE:
<223> OTHER INFORMATION: S356I Primer-F

<400> SEQUENCE: 13
cgggaattca atgcgtattc ccgta                                    25

<210> SEQ ID NO 14
<211> LENGTH: 22
<212> TYPE: DNA
<213> ORGANISM: Artificial Sequence
<220> FEATURE:
<223> OTHER INFORMATION: S356I Primer-R

<400> SEQUENCE: 14
attctcgagt cagtagggcc gc                                       22

<210> SEQ ID NO 15
<211> LENGTH: 19
<212> TYPE: DNA
<213> ORGANISM: Artificial Sequence
<220> FEATURE:
<223> OTHER INFORMATION: S356I Primer-M-F

<400> SEQUENCE: 15
ggcgaccgca tacctaccc                                           19

<210> SEQ ID NO 16
<211> LENGTH: 19
```

```
<212> TYPE: DNA
<213> ORGANISM: Artificial Sequence
<220> FEATURE:
<223> OTHER INFORMATION: S356I Primer-M-R

<400> SEQUENCE: 16
gggtaggtat gcggtcgcc                                           19

<210> SEQ ID NO 17
<211> LENGTH: 25
<212> TYPE: DNA
<213> ORGANISM: Artificial Sequence
<220> FEATURE:
<223> OTHER INFORMATION: S356L Primer-F

<400> SEQUENCE: 17
cgggaattca atgcgtattc ccgta                                    25

<210> SEQ ID NO 18
<211> LENGTH: 22
<212> TYPE: DNA
<213> ORGANISM: Artificial Sequence
<220> FEATURE:
<223> OTHER INFORMATION: S356L Primer-R

<400> SEQUENCE: 18
attctcgagt cagtagggcc gc                                       22

<210> SEQ ID NO 19
<211> LENGTH: 19
<212> TYPE: DNA
<213> ORGANISM: Artificial Sequence
<220> FEATURE:
<223> OTHER INFORMATION: S356L Primer-M-F

<400> SEQUENCE: 19
ggcgaccgcc tacctaccc                                           19

<210> SEQ ID NO 20
<211> LENGTH: 19
<212> TYPE: DNA
<213> ORGANISM: Artificial Sequence
<220> FEATURE:
<223> OTHER INFORMATION: S356L Primer-M-R

<400> SEQUENCE: 20
gggtaggtag gcggtcgcc                                           19

<210> SEQ ID NO 21
<211> LENGTH: 25
<212> TYPE: DNA
<213> ORGANISM: Artificial Sequence
<220> FEATURE:
<223> OTHER INFORMATION: S356G Primer-F

<400> SEQUENCE: 21
cgggaattca atgcgtattc ccgta                                    25

<210> SEQ ID NO 22
<211> LENGTH: 22
<212> TYPE: DNA
<213> ORGANISM: Artificial Sequence
<220> FEATURE:
<223> OTHER INFORMATION: S356G Primer-R

<400> SEQUENCE: 22
```

-continued

```
attctcgagt cagtagggcc gc                                            22

<210> SEQ ID NO 23
<211> LENGTH: 19
<212> TYPE: DNA
<213> ORGANISM: Artificial Sequence
<220> FEATURE:
<223> OTHER INFORMATION: S356G Primer-M-F

<400> SEQUENCE: 23
ggcgaccgcg gacctaccc                                                19

<210> SEQ ID NO 24
<211> LENGTH: 19
<212> TYPE: DNA
<213> ORGANISM: Artificial Sequence
<220> FEATURE:
<223> OTHER INFORMATION: S356G Primer-M-R

<400> SEQUENCE: 24
gggtaggtcc gcggtcgcc                                                19

<210> SEQ ID NO 25
<211> LENGTH: 25
<212> TYPE: DNA
<213> ORGANISM: Artificial Sequence
<220> FEATURE:
<223> OTHER INFORMATION: S356R Primer-F

<400> SEQUENCE: 25
cgggaattca atgcgtattc ccgta                                         25

<210> SEQ ID NO 26
<211> LENGTH: 22
<212> TYPE: DNA
<213> ORGANISM: Artificial Sequence
<220> FEATURE:
<223> OTHER INFORMATION: S356R Primer-R

<400> SEQUENCE: 26
attctcgagt cagtagggcc gc                                            22

<210> SEQ ID NO 27
<211> LENGTH: 19
<212> TYPE: DNA
<213> ORGANISM: Artificial Sequence
<220> FEATURE:
<223> OTHER INFORMATION: S356R Primer-M-F

<400> SEQUENCE: 27
ggcgaccgcc gacctaccc                                                19

<210> SEQ ID NO 28
<211> LENGTH: 19
<212> TYPE: DNA
<213> ORGANISM: Artificial Sequence
<220> FEATURE:
<223> OTHER INFORMATION: S356R Primer-M-R

<400> SEQUENCE: 28
gggtaggtcg gcggtcgcc                                                19

<210> SEQ ID NO 29
<211> LENGTH: 25
<212> TYPE: DNA
<213> ORGANISM: Artificial Sequence
```

```
<220> FEATURE:
<223> OTHER INFORMATION: S356N Primer-F

<400> SEQUENCE: 29
cgggaattca atgcgtattc ccgta                                               25

<210> SEQ ID NO 30
<211> LENGTH: 22
<212> TYPE: DNA
<213> ORGANISM: Artificial Sequence
<220> FEATURE:
<223> OTHER INFORMATION: S356N Primer-R

<400> SEQUENCE: 30
attctcgagt cagtagggcc gc                                                  22

<210> SEQ ID NO 31
<211> LENGTH: 19
<212> TYPE: DNA
<213> ORGANISM: Artificial Sequence
<220> FEATURE:
<223> OTHER INFORMATION: S356N Primer-M-F

<400> SEQUENCE: 31
ggcgaccgca atcctaccc                                                      19

<210> SEQ ID NO 32
<211> LENGTH: 19
<212> TYPE: DNA
<213> ORGANISM: Artificial Sequence
<220> FEATURE:
<223> OTHER INFORMATION: S356N Primer-M-R

<400> SEQUENCE: 32
gggtaggatt gcggtcgcc                                                      19

<210> SEQ ID NO 33
<211> LENGTH: 25
<212> TYPE: DNA
<213> ORGANISM: Artificial Sequence
<220> FEATURE:
<223> OTHER INFORMATION: S356C Primer-F

<400> SEQUENCE: 33
cgggaattca atgcgtattc ccgta                                               25

<210> SEQ ID NO 34
<211> LENGTH: 22
<212> TYPE: DNA
<213> ORGANISM: Artificial Sequence
<220> FEATURE:
<223> OTHER INFORMATION: S356C Primer-R

<400> SEQUENCE: 34
attctcgagt cagtagggcc gc                                                  22

<210> SEQ ID NO 35
<211> LENGTH: 19
<212> TYPE: DNA
<213> ORGANISM: Artificial Sequence
<220> FEATURE:
<223> OTHER INFORMATION: S356C Primer-M-F

<400> SEQUENCE: 35
ggcgaccgct gccctaccc                                                      19
```

<210> SEQ ID NO 36
<211> LENGTH: 19
<212> TYPE: DNA
<213> ORGANISM: Artificial Sequence
<220> FEATURE:
<223> OTHER INFORMATION: S356C Primer-M-R

<400> SEQUENCE: 36
gggtagggca gcggtcgcc                                            19

<210> SEQ ID NO 37
<211> LENGTH: 25
<212> TYPE: DNA
<213> ORGANISM: Artificial Sequence
<220> FEATURE:
<223> OTHER INFORMATION: S356Q Primer-F

<400> SEQUENCE: 37
cgggaattca atgcgtattc ccgta                                     25

<210> SEQ ID NO 38
<211> LENGTH: 22
<212> TYPE: DNA
<213> ORGANISM: Artificial Sequence
<220> FEATURE:
<223> OTHER INFORMATION: S356Q Primer-R

<400> SEQUENCE: 38
attctcgagt cagtagggcc gc                                        22

<210> SEQ ID NO 39
<211> LENGTH: 19
<212> TYPE: DNA
<213> ORGANISM: Artificial Sequence
<220> FEATURE:
<223> OTHER INFORMATION: S356Q Primer-M-F

<400> SEQUENCE: 39
ggcgaccgcc aacctaccc                                            19

<210> SEQ ID NO 40
<211> LENGTH: 19
<212> TYPE: DNA
<213> ORGANISM: Artificial Sequence
<220> FEATURE:
<223> OTHER INFORMATION: S356Q Primer-M-R

<400> SEQUENCE: 40
gggtaggttg gcggtcgcc                                            19

<210> SEQ ID NO 41
<211> LENGTH: 25
<212> TYPE: DNA
<213> ORGANISM: Artificial Sequence
<220> FEATURE:
<223> OTHER INFORMATION: S356H Primer-F

<400> SEQUENCE: 41
cgggaattca atgcgtattc ccgta                                     25

<210> SEQ ID NO 42
<211> LENGTH: 22
<212> TYPE: DNA
<213> ORGANISM: Artificial Sequence
<220> FEATURE:
<223> OTHER INFORMATION: S356H Primer-R -continued

<400> SEQUENCE: 42
attctcgagt cagtagggcc gc                                    22

<210> SEQ ID NO 43
<211> LENGTH: 19
<212> TYPE: DNA
<213> ORGANISM: Artificial Sequence
<220> FEATURE:
<223> OTHER INFORMATION: S356H Primer-M-F

<400> SEQUENCE: 43
ggcgaccgcc accctaccc                                        19

<210> SEQ ID NO 44
<211> LENGTH: 19
<212> TYPE: DNA
<213> ORGANISM: Artificial Sequence
<220> FEATURE:
<223> OTHER INFORMATION: S356H Primer-M-R

<400> SEQUENCE: 44
gggtagggtg gcggtcgcc                                        19

<210> SEQ ID NO 45
<211> LENGTH: 25
<212> TYPE: DNA
<213> ORGANISM: Artificial Sequence
<220> FEATURE:
<223> OTHER INFORMATION: S356K Primer-F

<400> SEQUENCE: 45
cgggaattca atgcgtattc ccgta                                 25

<210> SEQ ID NO 46
<211> LENGTH: 22
<212> TYPE: DNA
<213> ORGANISM: Artificial Sequence
<220> FEATURE:
<223> OTHER INFORMATION: S356K Primer-R

<400> SEQUENCE: 46
attctcgagt cagtagggcc gc                                    22

<210> SEQ ID NO 47
<211> LENGTH: 19
<212> TYPE: DNA
<213> ORGANISM: Artificial Sequence
<220> FEATURE:
<223> OTHER INFORMATION: S356K Primer-M-F

<400> SEQUENCE: 47
ggcgaccgca aacctaccc                                        19

<210> SEQ ID NO 48
<211> LENGTH: 19
<212> TYPE: DNA
<213> ORGANISM: Artificial Sequence
<220> FEATURE:
<223> OTHER INFORMATION: S356K Primer-M-R

<400> SEQUENCE: 48
gggtaggttt gcggtcgcc                                        19

<210> SEQ ID NO 49

<211> LENGTH: 25
<212> TYPE: DNA
<213> ORGANISM: Artificial Sequence
<220> FEATURE:
<223> OTHER INFORMATION: S356M Primer-F

<400> SEQUENCE: 49
cgggaattca atgcgtattc ccgta                                              25

<210> SEQ ID NO 50
<211> LENGTH: 22
<212> TYPE: DNA
<213> ORGANISM: Artificial Sequence
<220> FEATURE:
<223> OTHER INFORMATION: S356M Primer-R

<400> SEQUENCE: 50
attctcgagt cagtagggcc gc                                                 22

<210> SEQ ID NO 51
<211> LENGTH: 19
<212> TYPE: DNA
<213> ORGANISM: Artificial Sequence
<220> FEATURE:
<223> OTHER INFORMATION: S356M Primer-M-F

<400> SEQUENCE: 51
ggcgaccgca tgcctaccc                                                     19

<210> SEQ ID NO 52
<211> LENGTH: 18
<212> TYPE: DNA
<213> ORGANISM: Artificial Sequence
<220> FEATURE:
<223> OTHER INFORMATION: S356M Primer-M-R

<400> SEQUENCE: 52
gggtaggcat gcggtcgc                                                      18

<210> SEQ ID NO 53
<211> LENGTH: 25
<212> TYPE: DNA
<213> ORGANISM: Artificial Sequence
<220> FEATURE:
<223> OTHER INFORMATION: S356F Primer-F

<400> SEQUENCE: 53
cgggaattca atgcgtattc ccgta                                              25

<210> SEQ ID NO 54
<211> LENGTH: 22
<212> TYPE: DNA
<213> ORGANISM: Artificial Sequence
<220> FEATURE:
<223> OTHER INFORMATION: S356F Primer-R

<400> SEQUENCE: 54
attctcgagt cagtagggcc gc                                                 22

<210> SEQ ID NO 55
<211> LENGTH: 19
<212> TYPE: DNA
<213> ORGANISM: Artificial Sequence
<220> FEATURE:
<223> OTHER INFORMATION: S356F Primer-M-F

<400> SEQUENCE: 55

```
ggcgaccgct tccctaccc                                               19

<210> SEQ ID NO 56
<211> LENGTH: 19
<212> TYPE: DNA
<213> ORGANISM: Artificial Sequence
<220> FEATURE:
<223> OTHER INFORMATION: S356F Primer-M-R

<400> SEQUENCE: 56
gggtagggaa gcggtcgcc                                               19

<210> SEQ ID NO 57
<211> LENGTH: 25
<212> TYPE: DNA
<213> ORGANISM: Artificial Sequence
<220> FEATURE:
<223> OTHER INFORMATION: S356P Primer-F

<400> SEQUENCE: 57
cgggaattca atgcgtattc ccgta                                        25

<210> SEQ ID NO 58
<211> LENGTH: 22
<212> TYPE: DNA
<213> ORGANISM: Artificial Sequence
<220> FEATURE:
<223> OTHER INFORMATION: S356P Primer-R

<400> SEQUENCE: 58
attctcgagt cagtagggcc gc                                           22

<210> SEQ ID NO 59
<211> LENGTH: 19
<212> TYPE: DNA
<213> ORGANISM: Artificial Sequence
<220> FEATURE:
<223> OTHER INFORMATION: S356P Primer-M-F

<400> SEQUENCE: 59
ggcgaccgcc cacctaccc                                               19

<210> SEQ ID NO 60
<211> LENGTH: 19
<212> TYPE: DNA
<213> ORGANISM: Artificial Sequence
<220> FEATURE:
<223> OTHER INFORMATION: S356P Primer-M-R

<400> SEQUENCE: 60
gggtaggtgg gcggtcgcc                                               19

<210> SEQ ID NO 61
<211> LENGTH: 25
<212> TYPE: DNA
<213> ORGANISM: Artificial Sequence
<220> FEATURE:
<223> OTHER INFORMATION: S356W Primer-F

<400> SEQUENCE: 61
cgggaattca atgcgtattc ccgta                                        25

<210> SEQ ID NO 62
<211> LENGTH: 22
<212> TYPE: DNA
```

```
<213> ORGANISM: Artificial Sequence
<220> FEATURE:
<223> OTHER INFORMATION: S356W Primer-R

<400> SEQUENCE: 62
attctcgagt cagtagggcc gc                                          22

<210> SEQ ID NO 63
<211> LENGTH: 19
<212> TYPE: DNA
<213> ORGANISM: Artificial Sequence
<220> FEATURE:
<223> OTHER INFORMATION: S356W Primer-M-F

<400> SEQUENCE: 63
ggcgaccgct ggcctaccc                                              19

<210> SEQ ID NO 64
<211> LENGTH: 19
<212> TYPE: DNA
<213> ORGANISM: Artificial Sequence
<220> FEATURE:
<223> OTHER INFORMATION: S356W Primer-M-R

<400> SEQUENCE: 64
gggtaggcca gcggtcgcc                                              19
```

What is claimed is:

1. A method for treating cancer comprising administering a modified protein, a polynucleotide encoding the modified protein, a vector carrying the polynucleotide, or a virus or cell transformed with the vector, in a pharmaceutically effective amount to a subject in need thereof,
   wherein the modified protein is a Runx3 (Runt-related transcription factor 3) protein in which the 356$^{th}$ serine according to SEQ ID NO: 2 is substituted with an amino acid that cannot be phosphorylated by a kinase, and wherein the cancer is lung, stomach, or pancreatic cancer.

2. The method for treating cancer according to claim 1, wherein the amino acid that cannot be phosphorylated by a kinase is one or more selected from the group consisting of alanine (A), isoleucine (I), leucine (L) and valine (V).

3. The method for treating cancer according to claim 1, wherein SEQ ID NO: 2 is encoded by a polynucleotide represented by SEQ ID NO: 4.

4. The method for treating cancer according to claim 1, wherein the vector is linear DNA or plasmid DNA.

5. The method for treating cancer according to claim 1, wherein the virus is any one selected from the group consisting of retrovirus, adenovirus, herpes simplex virus and lentivirus.

6. The method for treating cancer according to claim 1, wherein the cell is bacterium.

7. The method for treating cancer according to claim 6, wherein the bacterium is *Listeria, Shigella, Salmonella*, or *E. coli*.

8. The method for treating cancer according to claim 1, wherein the modified protein binds BRD2 at least 10 times longer than wild-type Runx3 in vitro.

9. The method for treating cancer according to claim 1, wherein the cancer is lung cancer.

10. The method for treating cancer according to claim 9, wherein the amino acid that cannot be phosphorylated by a kinase is one or more selected from the group consisting of alanine (A), isoleucine (I), leucine (L) and valine (V).

11. The method for treating cancer according to claim 9, wherein the amino acid that cannot be phosphorylated is alanine (A).

* * * * *